United States Patent
Lewandrowski et al.

(10) Patent No.: US 9,283,267 B2
(45) Date of Patent: *Mar. 15, 2016

(54) FORMULATIONS OF TUMOUR-ASSOCIATED PEPTIDES BINDING TO HUMAN LEUKOCYTE ANTIGEN (HLA) CLASS I OR CLASS II MOLECULES FOR VACCINES

(75) Inventors: Peter Lewandrowski, Tuebingen-Unterjesingen (DE); Christian Flohr, Waldenbuch (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 76 days.

This patent is subject to a terminal disclaimer.

(21) Appl. No.: 13/346,197

(22) Filed: Jan. 9, 2012

(65) Prior Publication Data
US 2012/0107337 A1 May 3, 2012

Related U.S. Application Data

(62) Division of application No. 12/428,893, filed on Apr. 23, 2009.

(60) Provisional application No. 61/047,669, filed on Apr. 24, 2008.

(30) Foreign Application Priority Data

Apr. 30, 2008 (EP) .................................. 08008292

(51) Int. Cl.
| A61K 38/00 | (2006.01) |
| A61K 39/00 | (2006.01) |
| A61K 9/00  | (2006.01) |
| A61K 9/19  | (2006.01) |
| A61K 38/08 | (2006.01) |
| A61K 38/10 | (2006.01) |
| A61K 47/10 | (2006.01) |
| A61K 47/26 | (2006.01) |

(52) U.S. Cl.
CPC ............ *A61K 39/0011* (2013.01); *A61K 9/0019* (2013.01); *A61K 9/19* (2013.01); *A61K 38/08* (2013.01); *A61K 38/10* (2013.01); *A61K 47/10* (2013.01); *A61K 47/26* (2013.01); *Y10T 428/13* (2015.01)

(58) Field of Classification Search
CPC ....... A61K 38/08; A61K 38/00; A61K 47/00; C07K 5/00; C07K 7/06; C07K 16/30
See application file for complete search history.

(56) References Cited

U.S. PATENT DOCUMENTS

| 6,045,796 A | 4/2000 | Sriram et al. |
| 6,897,288 B1 | 5/2005 | Heidecker et al. |
| 7,312,196 B2 | 12/2007 | L'Italien et al. |
| 7,833,969 B2 | 11/2010 | Dengjel |
| 7,871,977 B2 | 1/2011 | Rischer et al. |
| 7,968,097 B2 | 6/2011 | Zeis |
| 8,119,139 B2 * | 2/2012 | Weinschenk et al. ...... 424/185.1 |
| 2003/0162711 A1 * | 8/2003 | Bjorn et al. ..................... 514/12 |
| 2007/0207956 A1 | 9/2007 | Jensen et al. |
| 2008/0125361 A1 | 5/2008 | Ludvigsen et al. |
| 2008/0207497 A1 | 8/2008 | Ramakrishna et al. |
| 2008/0242606 A1 | 10/2008 | Jiang |
| 2009/0274714 A1 | 11/2009 | Singh et al. |
| 2010/0029571 A1 * | 2/2010 | Rammensee et al. .......... 514/13 |
| 2010/0158931 A1 | 6/2010 | Weinschenk et al. |
| 2011/0002963 A1 | 1/2011 | Weinschenk |

FOREIGN PATENT DOCUMENTS

| EP | 1717245 | 11/2006 |
| EP | 1760088 | 3/2007 |
| EP | 1760089 | 3/2007 |
| WO | 9518145 | 7/1995 |
| WO | 2004016643 | 2/2004 |
| WO | 2007028573 | 3/2007 |
| WO | WO 2009138236 A1 * | 11/2009 |

OTHER PUBLICATIONS

European Search Report based on 09005725.8-2107 mailed Aug. 19, 2009.

Kirkin et al., "Melanoma-associated antigens recognized by cytotoxic T lymphocytes", 1998, APMIS, vol. 106, pp. 665-679, Printed in Denmark.

Chaux et al., "Estimation of the frequencies of anti-mage-3 cytolytic T-lymphocyte precursors in blood from individuals without cancer", Int J. Cancer, 1998, vol. 77, pp. 538-542, 1998 Wiley-Liss, Inc.

Sherman et al., "Strategies for tumor elimination by cytotoxic T lymphocytes", Critical Reviews in Immunol, 1998, vol. 18, pp. 47-54, Begell House, Inc.

Bossart et al., "Identification of HLA-A2-Restricted T-Cell Epitopes Derived from the MuC1 Tumor Antigen for Broadly Applicable Vaccine Therapies", Blood, Jun. 15, 1999, vol. 93, No. 12, pp. 4309-4317, The American Society of Hematology.

Mitchell et al., "Immunotherapy of malignant brain tumors", Immunological Reviews, Mar. 19, 2008, vol. 222, pp. 70-100 at 70 and 83-84, Blackwell Munksgaard, Printed in 2008 Singapore.

Bolliger et al., "Identification of a novel neuroligin in humans which binds to PSD-95 and has a widespread expression", Biochem. J., 2001, vol. 356, pp. 581-588, Biochemical Society (2001), Printed in Great Britain.

Lawson-Yuen et al., "Familial deletion within NLGN4 associated with autism and Tourette syndrome", European J. Human Genetics, 2008, vol. 16, pp. 614-618, Nature Publishing Group (Published online Jan. 30, 2008).

(Continued)

*Primary Examiner* — Hong Sang
(74) *Attorney, Agent, or Firm* — MMWV IP, LCC.

(57) ABSTRACT

The present invention relates to novel formulations of tumor-associated peptides binding to human leukocyte antigen (HLA) class I or II molecules as vaccines for the use in immunotherapeutic methods. In particular, the present invention relates to formulations for the immunotherapy of cancer, in particular renal and brain cancer, in particular glioma, especially glioblastoma cancer. The present invention furthermore relates to vaccine compositions for eliciting anti-tumor immune responses.

17 Claims, 20 Drawing Sheets

(56) References Cited

OTHER PUBLICATIONS

M. Kalos, "Tumor antigen-specific T cells and cancer immunotherapy: current issues and future prospects", Vaccine, 2003, vol. 21, pp. 781-786, 2002 Elsevier Science Ltd.

Lee et al., "Increased Vaccine-Specific T cell frequency after peptide-based vaccination correlates with increased susceptibility to In Vitro stimulation but does not lead to tumor regression", J. Immunol., Sep. 14, 1999, vol. 163, pp. 6292-6300, The American Association of Immunologists.

* cited by examiner

SEQUENCE LISTING

<160> NUMBER OF SEQ ID NOS: 23

<210> SEQ ID NO 1
<211> LENGTH: 16
<212> TYPE: PRT
<213> ORGANISM: Homo sapiens

<400> SEQUENCE: 1

Ser Gln Asp Asp Ile Lys Gly Ile Gln Lys Leu Tyr Gly Lys Arg Ser
1               5                   10                  15

<210> SEQ ID NO 2
<211> LENGTH: 9
<212> TYPE: PRT
<213> ORGANISM: Homo sapiens

<400> SEQUENCE: 2

Val Met Ala Gly Asp Ile Tyr Ser Val
1               5

<210> SEQ ID NO 3
<211> LENGTH: 9
<212> TYPE: PRT
<213> ORGANISM: Homo sapiens

<400> SEQUENCE: 3

Ser Val Ala Ser Thr Ile Thr Gly Val
1               5

<210> SEQ ID NO 4
<211> LENGTH: 9
<212> TYPE: PRT
<213> ORGANISM: Homo sapiens

<400> SEQUENCE: 4

Ala Leu Ala Asp Gly Val Gln Lys Val
1               5

<210> SEQ ID NO 5
<211> LENGTH: 9
<212> TYPE: PRT
<213> ORGANISM: Homo sapiens

<400> SEQUENCE: 5

Leu Leu Gly Ala Thr Cys Met Phe Val
1               5

<210> SEQ ID NO 6
<211> LENGTH: 9
<212> TYPE: PRT
<213> ORGANISM: Homo sapiens

<400> SEQUENCE: 6

Ser Val Phe Ala Gly Val Val Gly Val
1               5

<210> SEQ ID NO 7
<211> LENGTH: 9
<212> TYPE: PRT
<213> ORGANISM: Homo sapiens

<400> SEQUENCE: 7

Ala Leu Phe Asp Gly Asp Pro His Leu
1               5

<210> SEQ ID NO 8
<211> LENGTH: 9
<212> TYPE: PRT
<213> ORGANISM: Homo sapiens

<400> SEQUENCE: 8

Tyr Val Asp Pro Val Ile Thr Ser Ile
1               5

<210> SEQ ID NO 9
<211> LENGTH: 9
<212> TYPE: PRT
<213> ORGANISM: Homo sapiens

<400> SEQUENCE: 9

Ser Thr Ala Pro Pro Val His Asn Val
1               5

<210> SEQ ID NO 10
<211> LENGTH: 9
<212> TYPE: PRT
<213> ORGANISM: Homo sapiens

<400> SEQUENCE: 10

Leu Ala Ala Leu Pro His Ser Cys Leu
1               5

<210> SEQ ID NO 11
<211> LENGTH: 10
<212> TYPE: PRT
<213> ORGANISM: Homo sapiens

<400> SEQUENCE: 11

Phe Leu Pro Ser Asp Phe Phe Pro Ser Val
1               5                   10

<210> SEQ ID NO 12
<211> LENGTH: 9
<212> TYPE: PRT
<213> ORGANISM: Homo sapiens

<400> SEQUENCE: 12

Ala Leu Trp Ala Trp Pro Ser Glu Leu
1               5

<210> SEQ ID NO 13
<211> LENGTH: 15
<212> TYPE: PRT
<213> ORGANISM: Homo sapiens

<400> SEQUENCE: 13

Thr Leu Gly Glu Phe Leu Lys Leu Asp Arg Glu Arg Ala Lys Asn
1               5                   10                  15

<210> SEQ ID NO 14
<211> LENGTH: 9
<212> TYPE: PRT
<213> ORGANISM: Homo sapiens

<400> SEQUENCE: 14

Thr Met Leu Ala Arg Leu Ala Ser Ala
1               5

<210> SEQ ID NO 15

```
<211> LENGTH: 9
<212> TYPE: PRT
<213> ORGANISM: Homo sapiens

<400> SEQUENCE: 15

Leu Thr Phe Gly Asp Val Val Ala Val
1               5

<210> SEQ ID NO 16
<211> LENGTH: 9
<212> TYPE: PRT
<213> ORGANISM: Homo sapiens

<400> SEQUENCE: 16

Lys Ile Gln Glu Ile Leu Thr Gln Val
1               5

<210> SEQ ID NO 17
<211> LENGTH: 17
<212> TYPE: PRT
<213> ORGANISM: Homo sapiens

<400> SEQUENCE: 17

Thr Phe Ser Tyr Val Asp Pro Val Ile Thr Ser Ile Ser Pro Lys Tyr
1               5                   10                  15

Gly

<210> SEQ ID NO 18
<211> LENGTH: 9
<212> TYPE: PRT
<213> ORGANISM: Homo sapiens

<400> SEQUENCE: 18

Asn Leu Asp Thr Leu Met Thr Tyr Val
1               5

<210> SEQ ID NO 19
<211> LENGTH: 9
<212> TYPE: PRT
<213> ORGANISM: Homo sapiens

<400> SEQUENCE: 19

Gly Leu Trp His His Gln Thr Glu Val
1               5

<210> SEQ ID NO 20
<211> LENGTH: 9
<212> TYPE: PRT
<213> ORGANISM: Homo sapiens

<400> SEQUENCE: 20

Ala Ile Ile Asp Gly Val Glu Ser Val
1               5

<210> SEQ ID NO 21
<211> LENGTH: 9
<212> TYPE: PRT
<213> ORGANISM: Homo sapiens

<400> SEQUENCE: 21

Lys Val Phe Ala Gly Ile Pro Thr Val
1               5

<210> SEQ ID NO 22
```

```
<211> LENGTH: 9
<212> TYPE: PRT
<213> ORGANISM: Homo sapiens

<400> SEQUENCE: 22

Ala Met Thr Gln Leu Leu Ala Gly Val
1               5

<210> SEQ ID NO 23
<211> LENGTH: 9
<212> TYPE: PRT
<213> ORGANISM: Homo sapiens

<400> SEQUENCE: 23

Ser Leu Trp Ala Gly Val Val Val Leu
1               5
```

FORMULATIONS OF TUMOUR-ASSOCIATED PEPTIDES BINDING TO HUMAN LEUKOCYTE ANTIGEN (HLA) CLASS I OR CLASS II MOLECULES FOR VACCINES

RELATED APPLICATIONS

This application is a divisional application of U.S. application Ser. No. 12/428,893, filed on Apr. 23, 2009, which claims priority to U.S. provisional application 61/047,669, filed on Apr. 24, 2008, and EP application 08008292.8, filed on Apr. 30, 2008, each of which is incorporated herein by reference in their entirety.

FIELD OF THE INVENTION

The present invention relates to novel formulations of tumour-associated peptides binding to human leukocyte antigen (HLA) class I or II molecules as vaccines for the use in immunotherapeutic methods. In particular, the present invention relates to formulations for the immunotherapy of cancer, in particular renal and glioblastoma cancer. The present invention furthermore relates to vaccine compositions for eliciting anti-tumour immune responses.

For the purposes of the present invention, all references as cited herein are incorporated by reference in their entireties.

BACKGROUND OF THE INVENTION

A composition for injection consisting of peptides in the form of powder, and a diluent consisting of sodium hydrogen carbonate is disclosed in WO 2007/028573 for the vaccination of renal cell carcinoma. However, this formulation has various disadvantages. The main disadvantage is the poor solubility rendering its application very difficult during any application such as in clinical use.

To dissolve the powder in the composition, the vial containing the peptides to be dissolved and the diluent have to be shaken vigorously for three minutes, then submitted to ultrasound homogenation for one minute, and again to be shaken for one minute. This treatment cannot be applied by all physicians in their practices, as they often lack the equipment as required, and the archived mixture thus might not be homogeneous as required for an effective use.

An additional problem with the composition relates to the fact that, given the speed of dissolution of the active ingredients using sodium hydrogen carbonate in the given concentrations, the resulting solution can only be used for about 30 minutes.

Further, the characteristics of the above formulation change over time, which renders a safe use nearly impossible. After storage of the disclosed formulation for 12 months using different temperatures ranging from –20° C. to +25° C., no clear solution could be produced, even after using an ultrasound homogenator for several minutes.

Thus, there remains a need for novel peptide formulations with enhanced solubility and enhanced moistening of the lyophilisate, in order to provide a safe an effective preparation, in particular in case of an anti-cancer vaccine. The present invention fulfills this need.

SUMMARY OF THE INVENTION

The present invention in one preferred aspect thereof provides pharmaceutical compositions comprising between 2 and 18, preferably less than 15, more preferred less than 13, even more preferred 2 to 12 peptides and even more preferred 3 to 12 tumor associated peptides; wherein each peptide has a length of between 8 and 22 amino acids, preferably between 9 and 16 amino acids; wherein said peptides show a solubility in 90% acetic acid of at least 2.7 mg/mL; mannitol and poloxamer 188, wherein the ratio by weight of said peptide(s) to mannitol to poloxamer 188 is in the range including and between 1:5:1.5 to 1:8:2.2; or mannitol and TWEEN 80®, wherein the ratio by weight of peptides to mannitol to TWEEN 80® is in the range including and between 1:2:1.5 to 1:8:2.2.

In another preferred aspect thereof, the present invention provides a pharmaceutical composition according to claim 1, comprising at least two peptides, wherein said peptides comprise an amino acid sequence selected from the group consisting of SEQ ID NO: 1 to SEQ ID NO: 10, or SEQ ID NO: 12 to SEQ ID NO: 23; provided that the composition comprises at least one peptide comprising SEQ ID NO:1, SEQ ID NO: 2, SEQ ID NO: 12 or SEQ ID NO: 13 or a variant or salt thereof; and further comprising mannitol and poloxamer 188, wherein the ratio by weight of peptides to mannitol to poloxamer 188 is in the range including and between 1:5:1.5 to 1:8:2.2.

In yet another preferred aspect thereof, the present invention provides a pharmaceutical composition according to claim 1, comprising at least two peptides, wherein said peptides comprise an amino acid sequence selected from the group consisting of SEQ ID NO: 1 to SEQ ID NO: 10, or SEQ ID NO: 12 to SEQ ID NO: 23; provided that the composition comprises at least one peptide comprising SEQ ID NO: 1, SEQ ID NO: 2, SEQ ID NO: 12 or SEQ ID NO: 13 or a variant or salt thereof; and further comprising mannitol and TWEEN 80®, wherein the ratio by weight of peptides to mannitol to TWEEN 80® is in the range including and between 1:2:1.5 to 1:8:2.2.

Advantageously, the formulation according to the invention is suitable for stable formulations containing very hydrophobic peptides (for example IMA-CHI-001; SEQ ID NO: 23). This particular peptide, for example, is very insoluble in water and only slightly soluble in 90% acetic acid (solubility about 2.9 mg/mL). Surprisingly, it is now possible to formulate the peptide according to SEQ ID NO: 23 with any other peptide in another formulation that might be used for the application to a living being.

Therefore the application at hand discloses a formulation for formulating between 2 and 18 peptides, preferably less than 15, more preferred less than 13, even more preferred 2 to 12 peptides and even more preferred 3 to 12 peptides, with a peptide length between 8 and 22 amino acids, preferably between 9 and 16 amino acids, provided that the peptides show at least a solubility in 90% acetic acid of 2.7 mg/mL, preferably 2.9 mg/mL, and further comprising mannitol and poloxamer 188, wherein the ratio by weight of peptides to mannitol to poloxamer 188 is in the range including and between 1:5:1.5 to 1:8:2.2.

In a preferred embodiment of the pharmaceutical composition according to the present invention, the ratio by weight of peptides to mannitol to poloxamer 188 is in the range including and between 1:0:2 to 1:0:2.2.

Another preferred embodiment of the present invention provides a pharmaceutical composition as above, comprising at least two peptides wherein, said peptides comprise an amino acid selected from the group consisting of SEQ ID NO: 12 to SEQ ID NO: 23; provided that the composition comprises at least one peptide comprising SEQ ID NO: 12 or SEQ ID NO: 13 or a variant thereof; and further comprising mannitol and TWEEN 80®, wherein the preferred ratio by weight of peptides to mannitol to Tween 80® is in the range including and between 1:5:0.5 to 1:5:2.

Preferably the peptides of the present invention have an overall length of between 9 and 16 amino acids. The peptides may include non-peptide bonds.

In other preferred embodiments, the pharmaceutical compositions comprise peptides consisting of the amino acid sequences set forth in SEQ ID NO: 1 and/or SEQ ID NO: 2 and further comprise at least one peptide consisting of the amino acid sequence set forth in any one of SEQ ID NO: 3 to SEQ ID NO: 10.

In certain preferred embodiments, the pharmaceutical composition may further comprise a peptide comprising the amino acid sequence set forth in SEQ ID NO: 11, provided that said peptide is not the respective full-length tumour-associated polypeptide. In other embodiments, the pharmaceutical composition may further comprise a peptide that consists of the amino acid sequence set forth in SEQ ID NO: 11.

In other preferred embodiments, the pharmaceutical compositions comprise peptides consisting of the amino acid sequences set forth in SEQ ID NO: 12 and/or SEQ ID NO: 13 and further comprise at least one peptide consisting of the amino acid sequence set forth in any one of SEQ ID NO: 14 to SEQ ID NO: 23. In certain preferred embodiments, this pharmaceutical composition may further comprise a peptide comprising the amino acid sequence set forth in SEQ ID NO: 11, provided that said peptide is not the respective full-length tumour-associated polypeptide. In other embodiments, the pharmaceutical composition may further comprise a peptide that consists of the amino acid sequence set forth in SEQ ID NO: 11.

In certain embodiments, the peptides present in the composition are selected from tissue-, cancer-, and/or patient-specific peptides.

In further preferred embodiments, the pharmaceutical composition may further comprise at least one suitable adjuvant. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to, 1018 ISS, aluminum salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA), resimiquimod, ImuFact IMP321, Interleukins as IL-2, IL-13, IL-21, Interferon-alpha or -beta, or pegylated derivatives thereof, IS Patch, ISS, ISCOMATRIX®, ISCOMs, JUVIMMUNE®, LipoVac, MALP2, MF59, monophosphoryl lipid A, MONTANIDE® IMS 1312, MONTANIDE® ISA 206, MONTANIDE® ISA 50V, MONTANIDE® ISA-51, water-in-oil and oil-in-water emulsions, OK-432, OM-174, OM-197-MP-EC, ONTAK®, OspA, PEPTEL® vector system, PLG and dextran microparticles, resimiquimod, SRL172, Virosomes and other Virus-like particles, YF-17D, VEGF trap, R848, beta-glucan, Pam3Cys, Aquila's QS21 STIMULON®, which is derived from saponin, mycobacterial extracts and synthetic bacterial cell wall mimics, and other proprietary adjuvants such as Ribi's DETOXT™, QUIL™, OR SUPERFOS™. Adjuvants such as Freund's or GM-CSF are preferred. Several immunological adjuvants (e.g., MF59) specific for dendritic cells and their preparation have been described previously (Dupuis M et al 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting aso immunoadjuvants (e.g., IL-12, IL-15, IL-23, IL-7, IFN-alpha, IFN-beta) (Gabrilovich et al 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg et al 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by MOLOGEN® (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and AMPLIGEN®, non-CpG bacterial DNA or RNA as well as immunoactive small molecules and antibodies such as cyclophosphamide, sunitinib, Bevacizumab, CELEBREX®, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation. Preferred adjuvants are dSLIM, interferon-alpha, -beta, CpG7909, IC31, imiquimod, resimiquimod, PEVITER®, RNA, tadalafil, temozolomide, and JUVIMMUNE®.

Preferred adjuvants are dSLIM, BCG, OK432, imiquimod, resimiquimod, GMCSF, interferon-alpha, PEVITER® and JUVIMMUNE® or combinations thereof.

In a preferred embodiment the pharmaceutical composition according to the invention the adjuvant is selected from the group consisting of colony-stimulating factors, such as Granulocyte Macrophage Colony Stimulating Factor (GM-CSF, sargramostim), imiquimod, resimiquimod, and interferon-alpha.

In a preferred embodiment the pharmaceutical composition according to the invention the adjuvant is selected from the group consisting of colony-stimulating factors, such as Granulocyte Macrophage Colony Stimulating Factor (GM-CSF, sargramostim), immiquimod and resiquimod.

In a preferred embodiment of the pharmaceutical composition according to the invention, the adjuvant is imiquimod or resimiquimod.

This composition can be used for parenteral administration, such as subcutaneous, intradermal, intramuscular or oral administration. The peptides can also be administered together with immune stimulating substances, such as cytokines.

The pharmaceutical compositions of the invention may be used as an anti-cancer vaccine.

The present invention also encompasses a kit comprising at least one of the above peptides, and/or the above pharmaceutical composition, either pre-prepared or in separate containers or vials for on-site admixture.

Preferred is a kit comprising: (a) a container containing a pharmaceutical composition according to the invention, in solution or in lyophilized form; (b) optionally, a second container containing a diluent or reconstituting solution for said lyophilized formulation and/or at least one adjuvant; and (c) optionally, instructions for (i) use of the solution, or (ii) reconstitution, and/or use of said lyophilized formulation.

Further preferred is a kit according to the invention, further comprising one or more of (i) a buffer, (ii) a diluent, (iii) a filter, (iv) a needle, and (v) a syringe.

Figure 1:
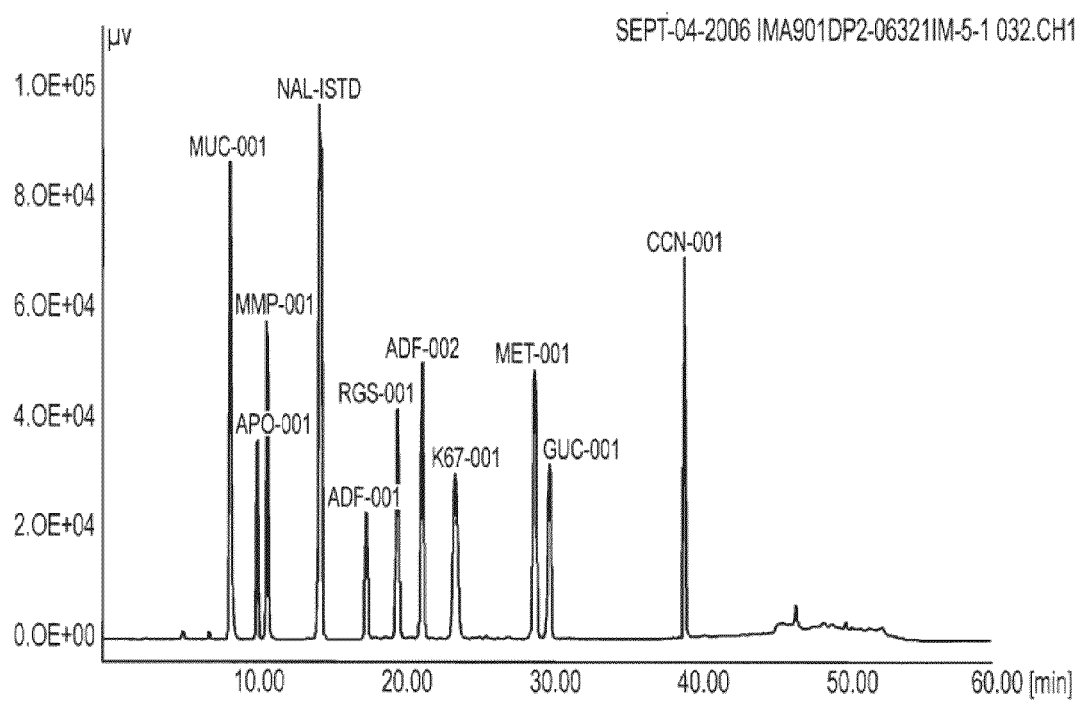
FIG. 1: Analytical HPLC Chromatogram of peptides (SEQ ID NO: 1-11) containing beta-naphthylalanine (NAL) as internal standard.
Figure 2:
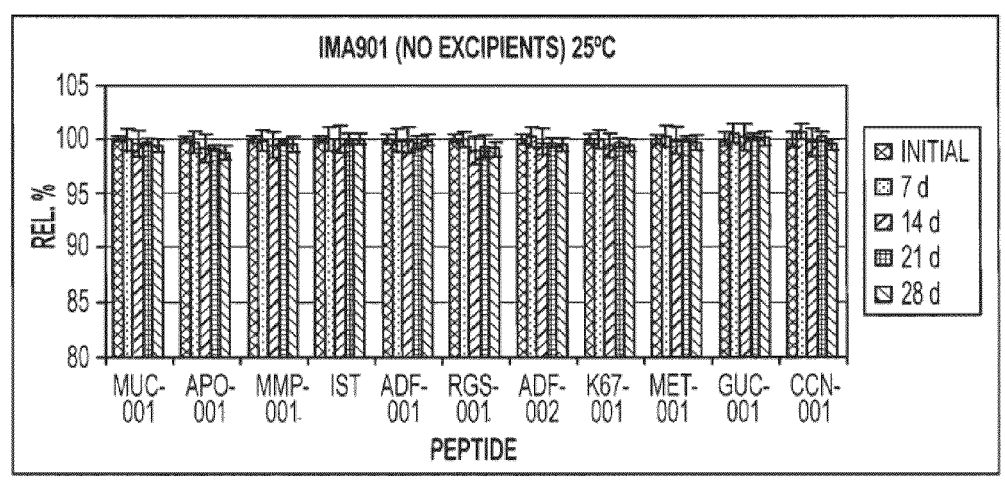
FIG. 2: Stability of formulation 1 (control) without any excipients at +25° C.
Figure 3:
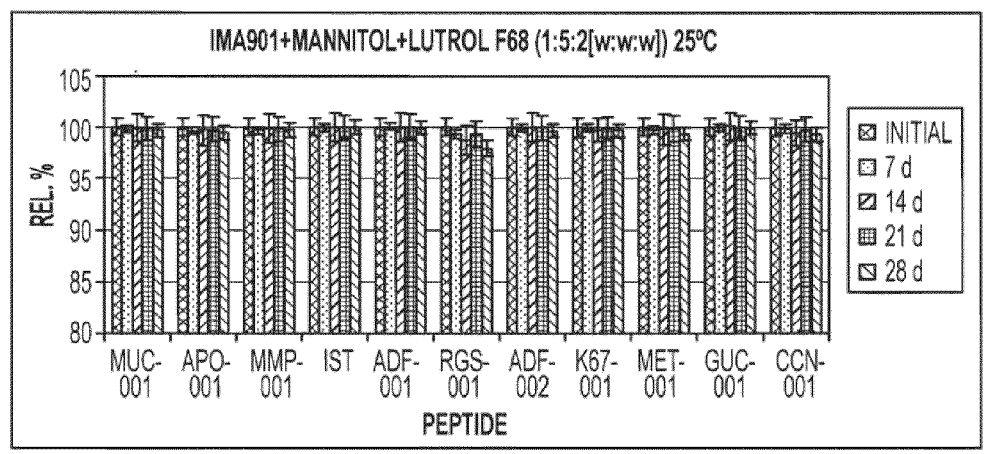
FIG. 3: Stability of formulation 2 according to the invention with mannitol and LUTROL F68® (Poloxamer 188) at +25° C.
Figure 4:
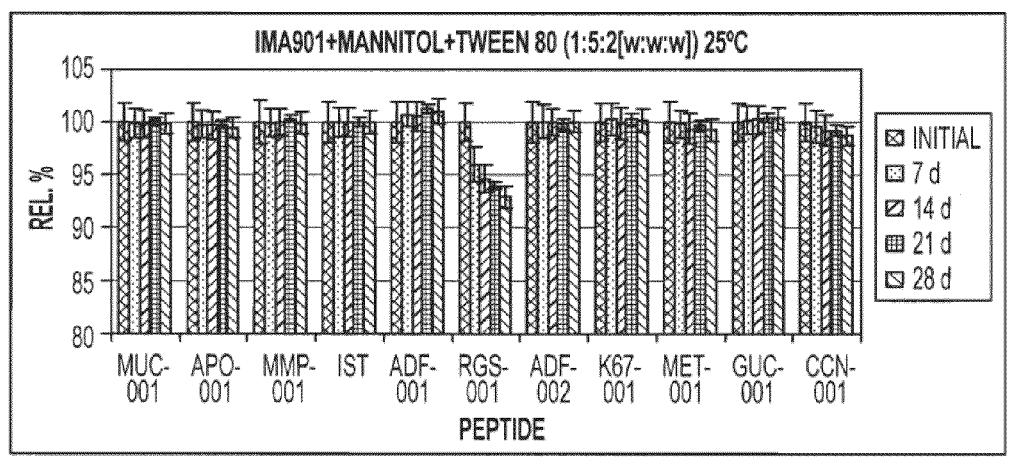
FIG. 4: Stability of formulation 3 according to the invention with mannitol and TWEEN 80® at +25° C.
Figure 5:
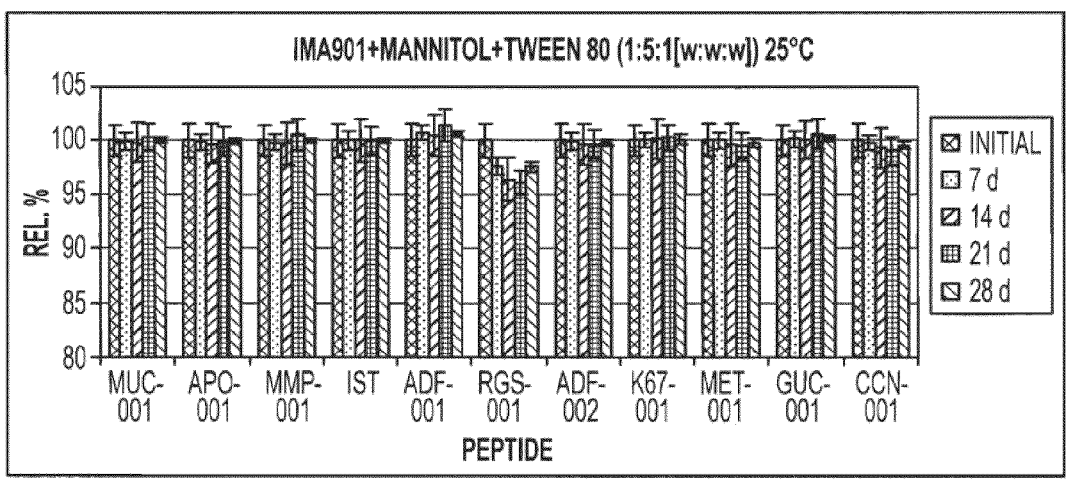
FIG. 5: Stability of formulation 4 according to the invention with mannitol and TWEEN 80® at +25° C.
Figure 6:
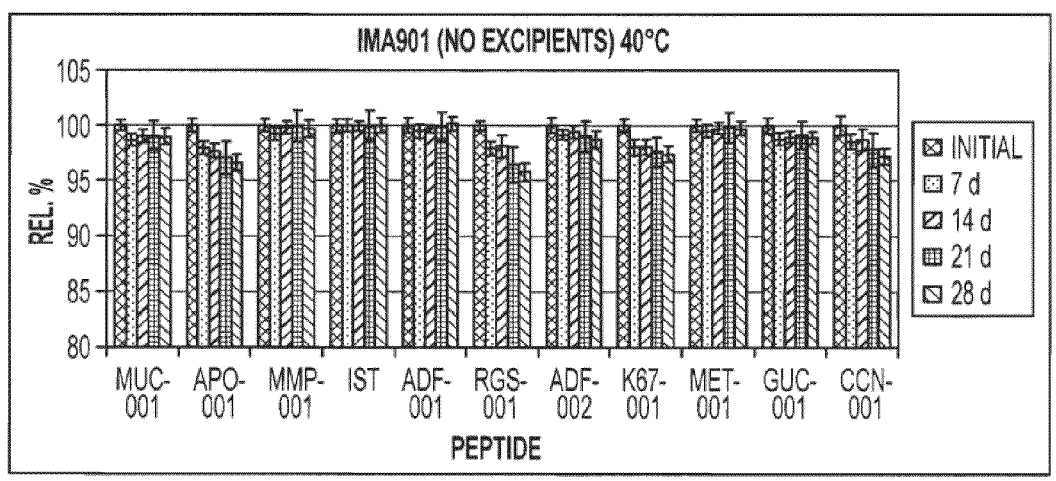
FIG. 6: Stability of formulation 1 (control) without any excipients at +40° C.
Figure 7:
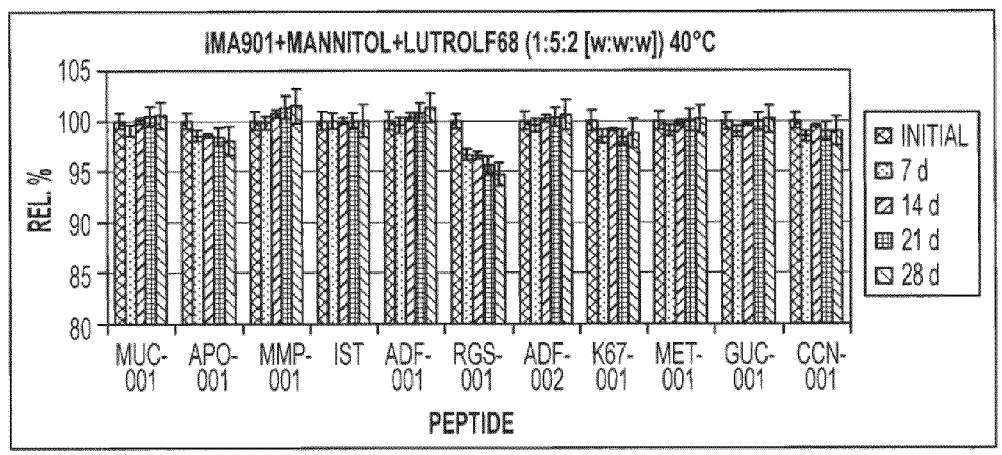
FIG. 7: Stability of formulation 2 according to the invention with mannitol and LUTROL F68® (Poloxamer 188) at +40° C.
Figure 8:
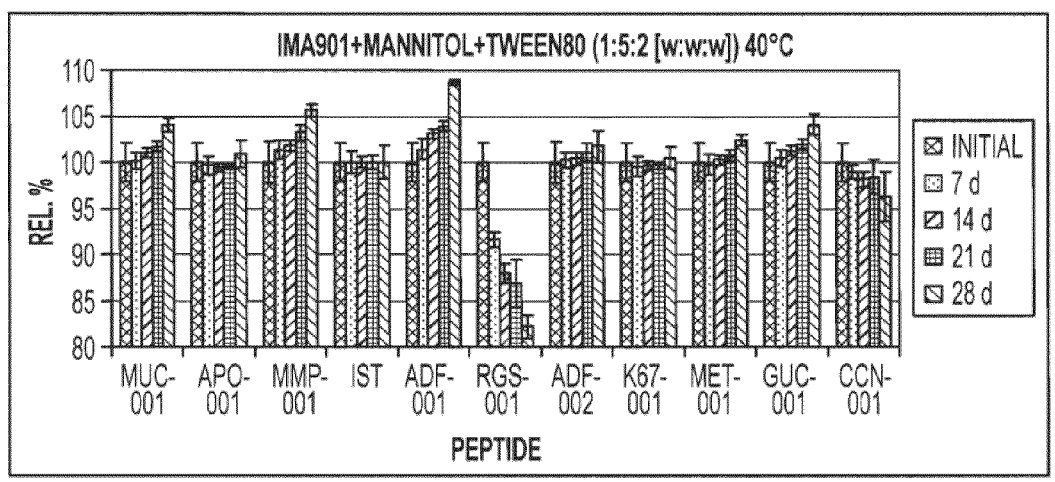
FIG. 8: Stability of formulation 3 according to the invention with mannitol and TWEEN 80® at +40° C.
Figure 9:
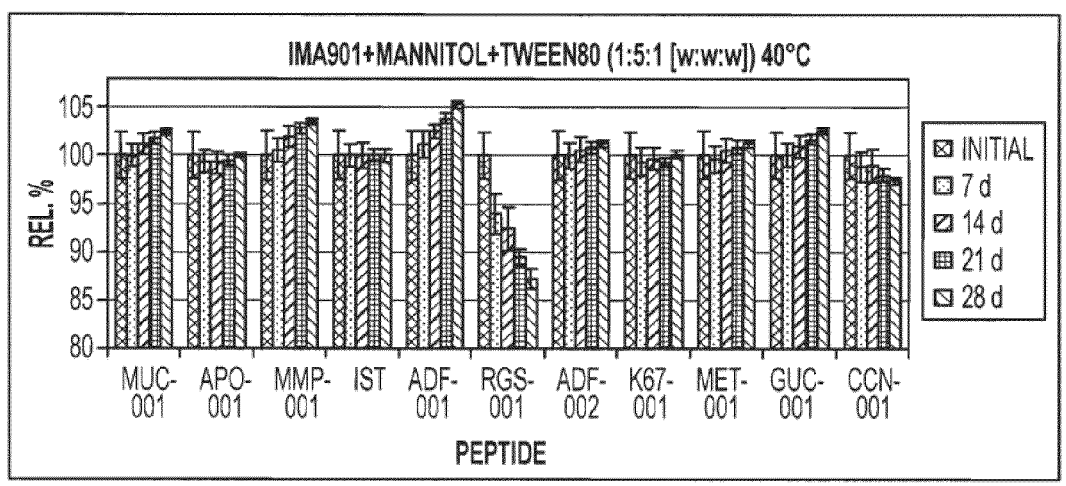
FIG. 9: Stability of formulation 4 according to the invention with mannitol and TWEEN 80® at +40° C.
Figure 10:
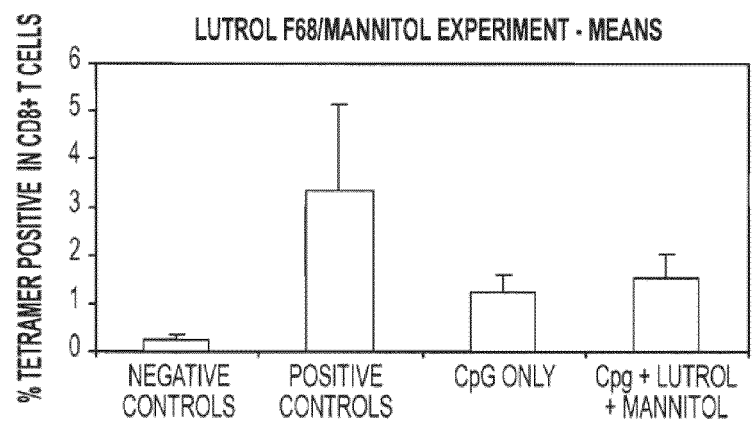
FIG. 10: Effects of the excipients Poloxamer 188 (LUTROL F68® available from BASF Ludwigshafen, Germany) and mannitol on CD8+ T cell priming in vivo. Mice were sacrificed 9 days after immunization, spleen cells were collected, stained with tetramer and analyzed by flow cytometry. Percentage of tetramer positive cells among all CD8+ T cells are shown with error bars showing the standard deviation of means. All three peptide-immunized groups are significantly different from the negative controls as analyzed by two-tailed, unpaired student's T-test (p<0.05). The groups with and without Poloxamer (LUTROL F68®)/mannitol do not differ significantly (p=0.49).
Figure 11:
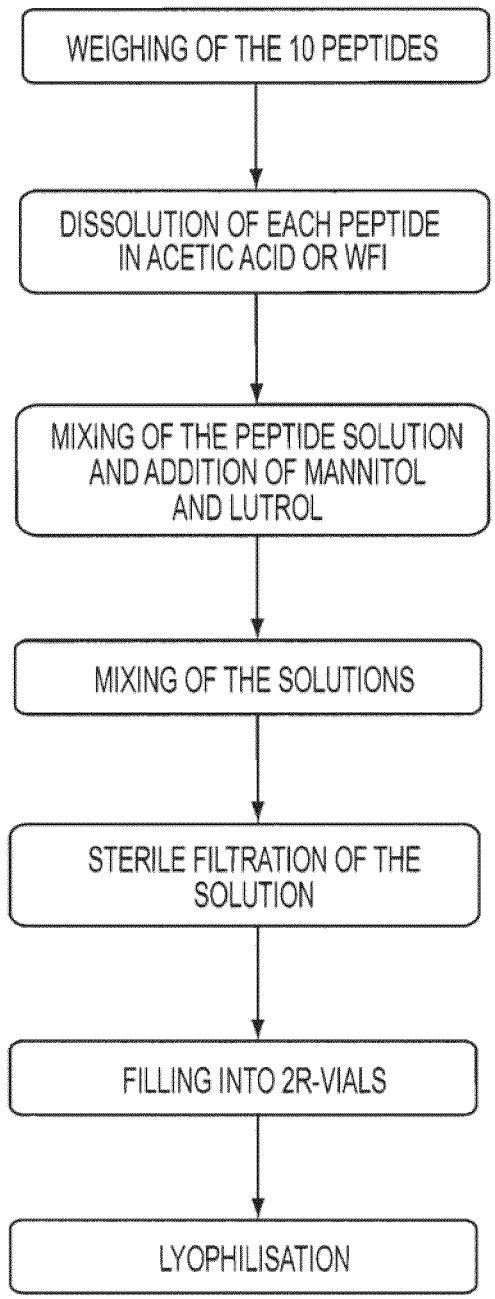
FIG. 11: Manufacturing process described in example 2.
Figure 12:
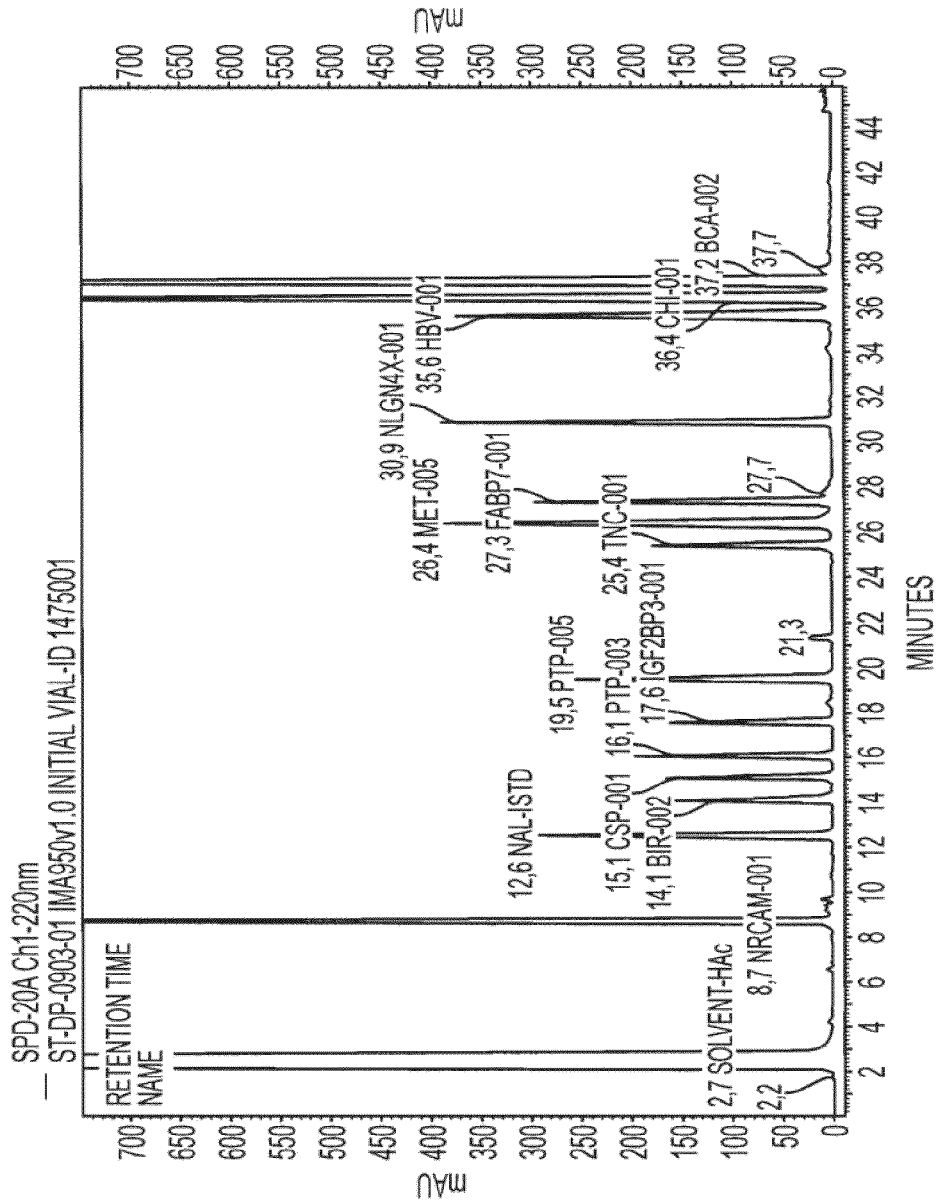
FIG. 12: Analytical HPLC Chromatogram of peptides (SEQ ID NO: 11-23) containing beta-naphthylalanine (NAL) as internal standard.
Figure 13:
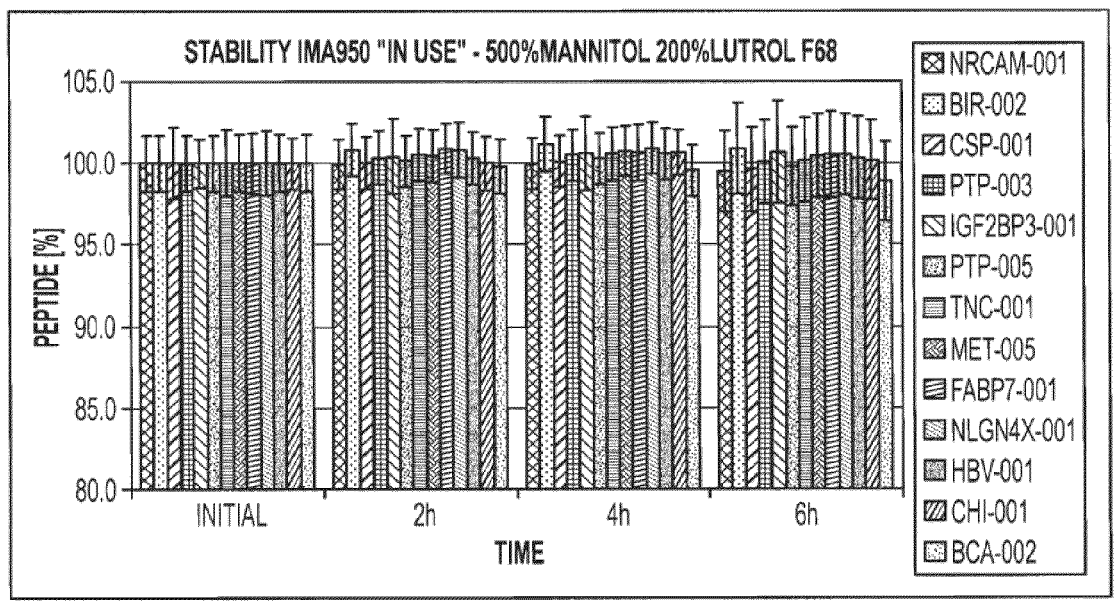
FIG. 13: Stability "In use" of peptides of SEQ ID NO: 11 to 23 with Mannitol/LUTROL F68®.
Figure 14:
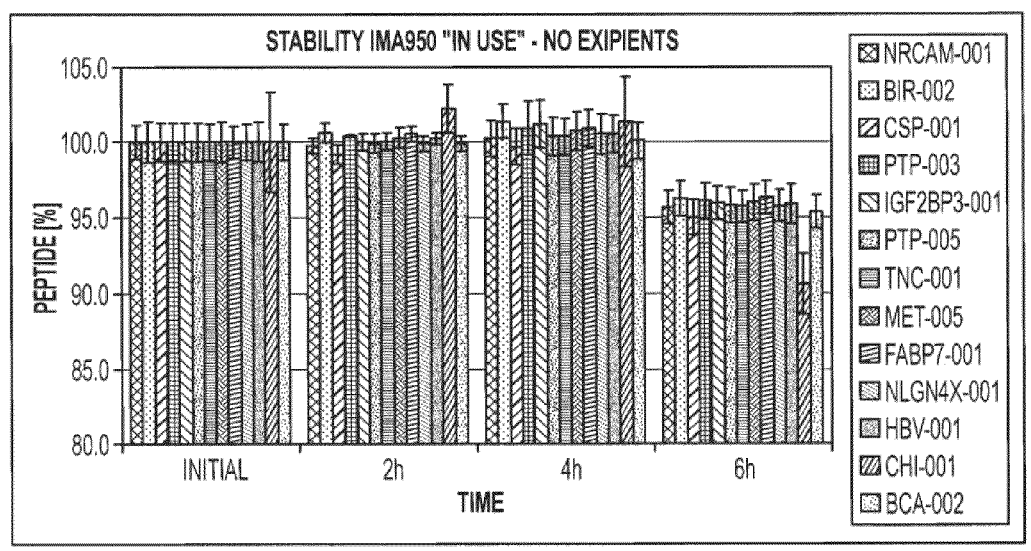
FIG. 14: Stability "In use" of peptides of SEQ ID NO: 11 to 23 with no excipients.
Figure 15:
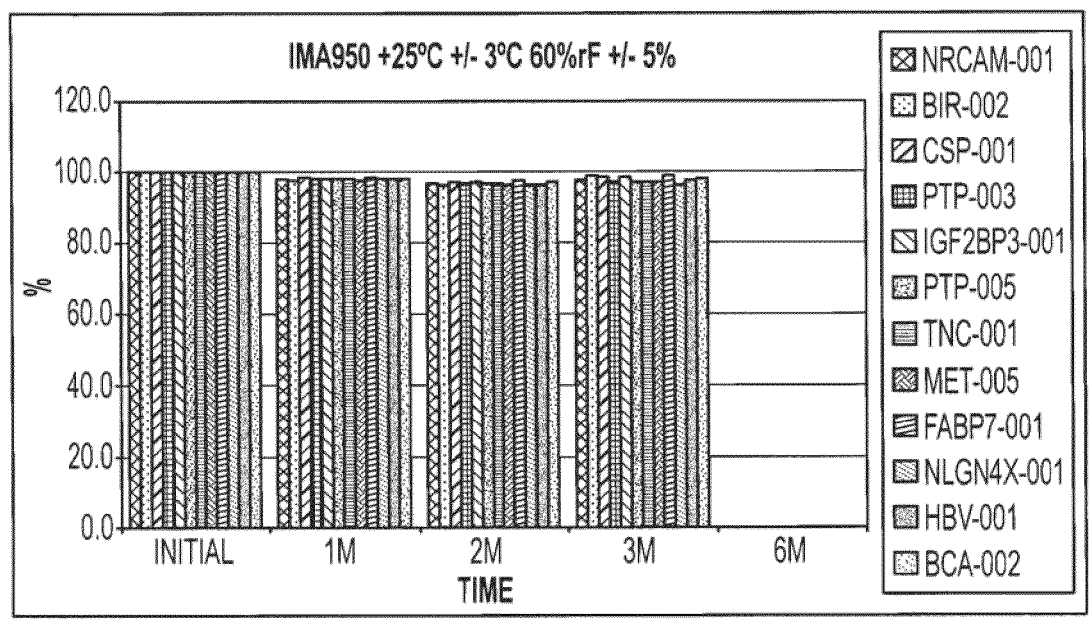
FIG. 15: Stability of peptides of SEQ ID NO: 11 to 22 with Mannitol/LUTROL F68® at +25° C.
Figure 16:
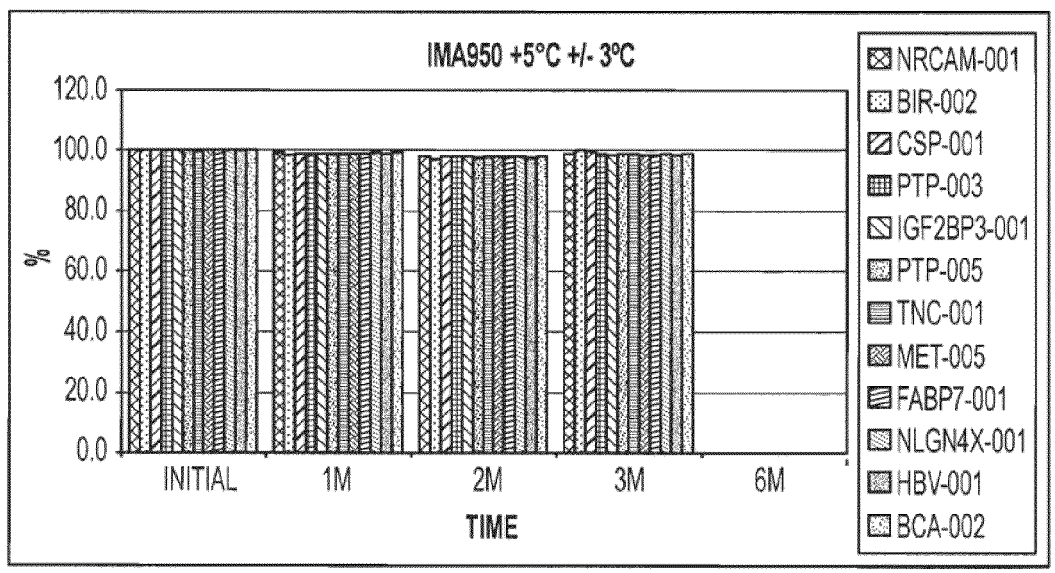
FIG. 16: Stability of peptides of SEQ ID NO: 11 to 22 with Mannitol/LUTROL F68® at +5° C.
Figure 17:
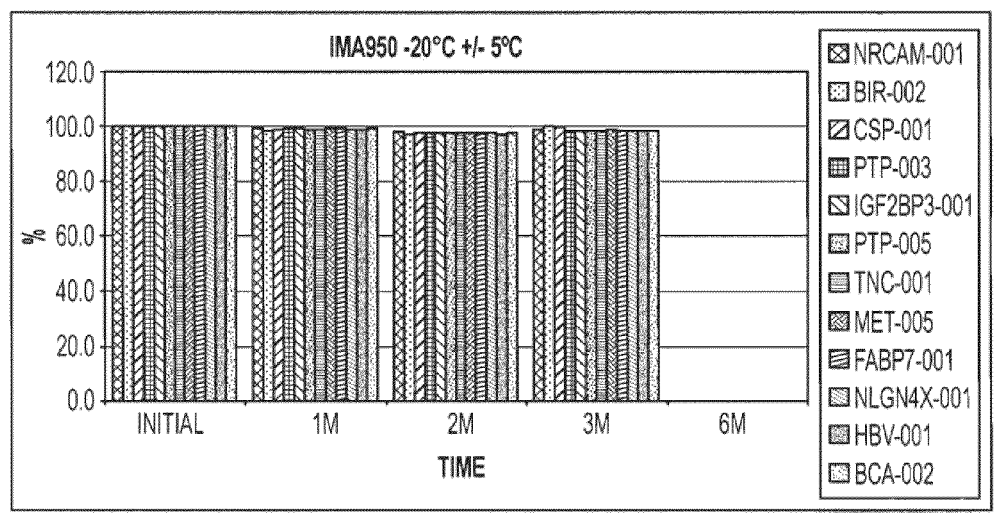
FIG. 17: Stability of peptides of SEQ ID NO: 11 to 22 with Mannitol/LUTROL F68® at −20° C.
Figure 18:
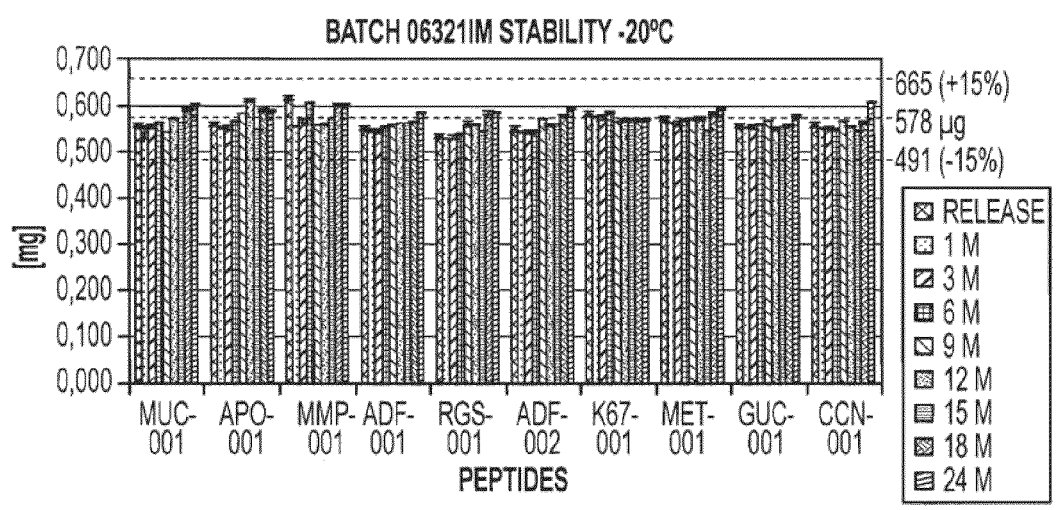
FIG. 18: 24 Month stability data at −20° C. for the formulation described in Example 2.
Figure 19:
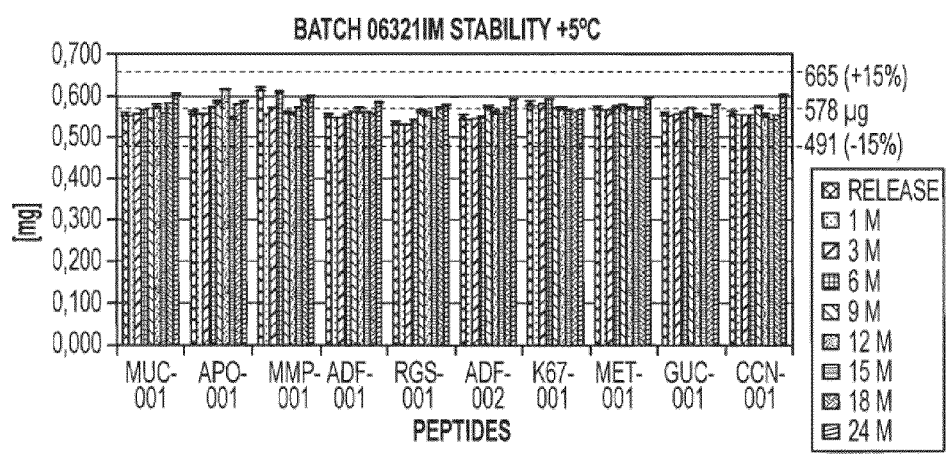
FIG. 19: 24 Month stability data at +5° C. for the formulation described in Example 2.
Figure 20:
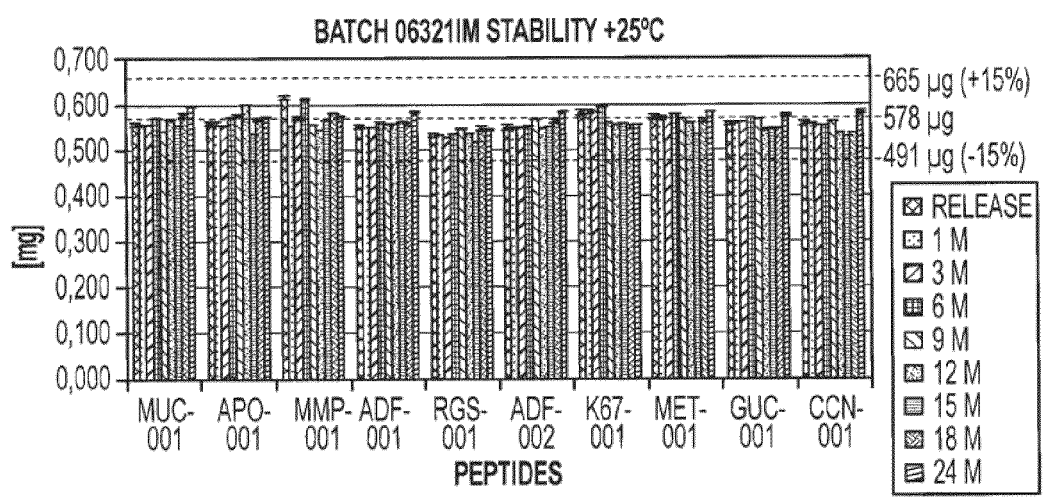
FIG. 20: 24 Month stability data at +25° C. for the formulation described in Example 2.

The sequence listing shows peptides (SEQ ID NO: 1 to 23) that are used in formulations according to the present invention.

DETAILED DESCRIPTION OF THE INVENTION

The present invention provides pharmaceutical compositions useful as a vaccine, wherein said pharmaceutical composition comprises various tumour-associated peptides (TUMAPs) in addition to either a mixture of mannitol and TWEEN 80®, or a mixture of mannitol and poloxamer 188, which mixtures provide stability and solubility for said composition.

Polyoxyethylene (20) sorbitan monooleate is the corresponding IUPAC name for TWEEN 80®.

"Pharmaceutical composition" as used herein preferably are a lyophilized formulation comprising peptides, mannitol, and TWEEN 80® or the peptides, mannitol and poloxamer 188 or preferably are a reconstituted-liquid composition. As such, the term "pharmaceutical compositions" as used herein maybe also refer to the lyophilized formulation to indicate that the composition is present in a lyophilized form.

Preferably, the peptides in the pharmaceutical compositions comprise at least one of the peptides set forth in SEQ ID NO: 1 to 10, which are located and have been identified on primary renal cancer cells or at least one of the peptides set forth in SEQ ID NO: 11 to 22 and optionally SEQ ID NO: 23, which are located and have been identified on primary glioma cancer cells.

In other preferred embodiments, the pharmaceutical compositions comprise peptides consisting of the amino acid sequences set forth in SEQ ID NO: 12 and/or SEQ ID NO: 13 and further comprise at least one peptide consisting of the amino acid sequence set forth in any one of SEQ ID NO: 14 to SEQ ID NO: 23.

The peptide sets includes HLA class I and class II peptides. Preferably, a pharmaceutical composition of the present invention comprises a peptide as set forth in SEQ ID NO:1 and/or SEQ ID NO:2 and/or at least one other peptide comprising SEQ ID NO: 3-10 or a peptide as set forth in SEQ ID NO:12 and/or SEQ ID NO:13 and/or at least one other peptide comprising SEQ ID NO: 11 and 14-23.

The pharmaceutical compositions comprise the peptides either in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties that may be present on a peptide are prepared using a pharmaceutically acceptable base such as sodium hydroxide, potassium hydroxide, ammonium hydroxide, calcium hydroxide, trimethylamine or the like.

In an especially preferred embodiment the pharmaceutical compositions comprise the peptides as salts of acetic acid (acetates) or hydrochloric acid (chlorides).

In an even more preferred embodiment, the pharmaceutical compositions according to the invention comprise SEQ ID NO: 5 as a chloride and all other peptides as acetates.

Pharmaceutical compositions of the present invention may also contain at least one peptide to serve as a positive control peptide as an immune marker to test the efficiency of the intradermal administration. One such exemplary peptide is derived from HBV core antigen (SEQ ID NO:11).

In one particular embodiment, the pharmaceutical composition comprises 11 different peptides, each consisting of the amino acid sequences set forth in SEQ ID NO: 1 to 11. (See Table 1). Preferably, each peptide in the pharmaceutical composition is present in an amount of between about 1500 µg to about 75 µg, preferably between about 1000 µg to about 750 µg and more preferably between about 500 µg to about 600 µg, and most preferably about 578 µg. Preferably, each peptide is purified by HPLC and ion exchange chromatography, and appears as a white to off-white powder.

In another particular embodiment, the pharmaceutical composition comprises 12 different peptides, each consisting of the amino acid sequences set forth in SEQ ID NO: 11 to 22 and optionally, the sequence set forth in SEQ ID NO: 23. (See Table 1). Preferably, each peptide in the pharmaceutical composition is present in an amount of between about 1500 µg to about 75 µg, preferably between about 1000 µg to about 750 µg and more preferably between about 500 µg to about 600 µg, and most preferably about 578 µg. Preferably, each peptide is purified by HPLC and ion exchange chromatography, and appears as a white to off-white powder.

TABLE 1

Preferred peptides in pharmaceutical compositions of the present invention

| Internal Sequence ID | Antigen | Sequence | SEQ ID NO: |
|---|---|---|---|
| IMA-MMP-001 | Matrix metalloproteinase 7 | SQDDIKGIQKLYGKRS | 1 |
| IMA-ADF-002 | Adipophilin | VMAGDIYSV | 2 |
| IMA-ADF-001 | Adipophilin | SVASTITGV | 3 |
| IMA-APO-001 | Apolipoprotein L1 | ALADGVQKV | 4 |
| IMA-CCN-001 | Cyclin D1 | LLGATCMFV | 5 |
| IMA-GUC-001 | GUCY1A3 | SVFAGVVGV | 6 |
| IMA-K67-001 | KIAA0367 | ALFDGDPHL | 7 |
| IMA-MET-001 | c-met proto-oncogene | YVDPVITSI | 8 |
| IMA-MUC-001 | MUC1 | STAPPVHNV | 9 |
| IMA-RGS-001 | RGS-5 | LAALPHSCL | 10 |
| IMA-HBV-001 | HBV | FLPSDFFPSV | 11 |
| IMA-BCA-002 | Brevican (NP_068767, 478-486) | ALWAWPSEL | 12 |
| IMA-BIR-002 | Baculoviral IAP repeat-containing 5 (NP_001159, 97-111) | TLGEFLKLDRERAKN | 13 |
| IMA-CSP-001 | Chondroitin sulfate proteoglycan 4 (NP_001888, 21-29) | TMLARLASA | 14 |
| IMA-FABP7-001 | Fatty acid binding protein 7, brain (NP_001437, 118-126) | LTFGDVVAV | 15 |
| IMA-IGF2BP3-001 | Insulin-like growth factor 2 mRNA binding protein 3 (NP_006538, 552-560) | KIQEILTQV | 16 |
| IMA-MET-005 | Met proto-oncogene (NP_000236, 651-667) | TFSYVDPVITSISPKYG | 17 |
| IMA-NLGN4X-001 | Neuroligin 4, X-linked (NP_065793, 131-139) | NLDTLMTYV | 18 |
| IMA-NRCAM-001 | Neuronal cell adhesion molecule (NP_001032209, 692-700) | GLWHHQTEV | 19 |

TABLE 1-continued

Preferred peptides in pharmaceutical compositions of the present invention

| Internal Sequence ID | Antigen | Sequence | SEQ ID NO: |
|---|---|---|---|
| IMA-PTP-003 | Protein tyrosine phosphatise, receptor-type, Z polypeptide 1 (NP_002842, 195-203) | AIIDGVESV | 20 |
| IMA-PTP-005 | Protein tyrosine phosphatise, receptor-type, Z polypeptide 1 (NP_002842, 1347-1355) | KVFAGIPTV | 21 |
| IMA-TNC-001 | Tenascin C (NP_002151, 3-11) | AMTQLLAGV | 22 |
| IMA-CHI-001 | | SLWAGVVVL | 23 |

The term "peptide" is used herein to designate a series of amino acid residues, connected one to the other typically by peptide bonds between the alpha-amino and carbonyl groups of the adjacent amino acids. The peptides are typically 9 amino acids in length for MHC class I and longer (15 or 16 amino acids) for MHC class II, but can be as short as 8 amino acids in length, and as long as 16 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to protein molecules of longer than about 30 residues in length.

A peptide, oligopeptide, protein, or polynucleotide coding for such a molecule is "immunogenic" (and thus an "immunogen" within the present invention), if it is capable of inducing an immune response. In the case of the present invention, immunogenicity is more specifically defined as the ability to induce a CTL-mediated response. Thus, an "immunogen" would be a molecule that is capable of inducing an immune response, and in the case of the present invention, a molecule capable of inducing a CTL response.

A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length. T cell epitopes that bind to class II MHC molecules are typically 12-30 amino acids in length. In the case of epitopes that bind to class II MHC molecules, the same T cell epitope may share a common core segment, but differ in the length of the carboxy- and amino-terminal flanking sequences due to the fact that the ends of the peptide molecule are not buried in the structure of the class II MHC molecule peptide-binding groove as they are in the class I MHC molecule peptide-binding groove.

There are three different genetic loci that encode for class I MHC molecules: HLA-A, HLA-B, and HLA-C. HLA-A1, HLA-A2, and HLA-A11 are examples of different class I MHC molecules that can be expressed from these loci.

As used herein, the terms "portion," "segment," and "fragment," when used in relation to polypeptides, refer to a continuous sequence of residues, such as amino acid residues, which sequence forms a subset of a larger sequence. For example, if a polypeptide was subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to 23, which correspond to the naturally occurring, or "parent" proteins of the SEQ ID NO: 1 to 23. When used in relation to polynucleotides, such terms refer to the products produced by treatment of said polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence, and (ii) each gap in the Reference Sequence, and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence even though alignments may exist in which the herein above calculated Percent Identity is less than the specified Percent Identity.

The peptides in the pharmaceutical compositions of the present invention can be modified by the substitution of one or more residues at different, possibly selective, sites within the peptide chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 5—large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater immunogenic activity as defined below, then combinations of those substitutions will be tested to determine if the combined substitutions result in additive or synergistic effects on the immunogenicity of the peptide. At most, no more than four positions within the peptide would simultaneously be substituted.

Preferably, when the CTLs specific for a peptide of SEQ ID NO: 1 to 23 are tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 μM, and most preferably no more than about 10 μM. It is also preferred that the substituted peptide be recognized by CTLs from more than one individual, at least two, and more preferably three individuals.

Mucin-1 (MUC1) is a highly glycosylated type I transmembrane glycoprotein that is abundantly overexpressed on the cell surface of many human adenocarcinomas like breast and ovarian cancers. Aberrant deglycosylation in malignancies is common and unmasks epitopes in tumour cells that might not be presented on normal cells. Moreover, MUC1 expression has been demonstrated in multiple myeloma and some B-cell Non-Hodgkin lymphomas. Several recent reports (Apostolopoulos V and McKenzie I F. Cellular mucins: targets for immunotherapy. Crit Rev. Immunol. 14:293-309 (1994); Finn O J, Jerome K R, Henderson R A, Pecher G, Domenech N, Magarian-Blander J, and Barratt-Boyes S M. MUC-1 epithelial tumor mucin-based immunity and cancer vaccines. Immunol. Rev. 145:61-89 (1995); Barnd 1989; Takahashi 1994; Noto 1997) demonstrated that cytotoxic MHC-unrestricted T-cells from ovarian, breast, pancreatic, and multiple myeloma tumours can recognize epitopes of the MUC1 protein core localized in the tandem repeat. Two HLA-A2-restricted T-cell epitopes derived from the MUC1 protein have been identified (Brossart 1999, EP 1484397). One peptide is derived from the tandem repeat region of the MUC1 protein. The second peptide is localized within the signal sequence of MUC1. Induction of cytotoxic T-lymphocyte responses in vivo after vaccinations with peptide-pulsed dendritic cells in patients with advanced breast or ovarian cancer using those peptides has been successful (Brossart 2000) (Wierecky 2005). With respect to renal cell carcinoma, MUC1 expression is common in conventional tumours and has been reported to be associated with tumour grade and stage. For MUC1, protein overexpression is not correlated to mRNA overexpression.

Adipophilin is a marker for specialized differentiated cells containing lipid droplets and for diseases associated with fat-accumulating cells (Heid 1998). Adipophilin occurs in a wide range of cultured cell lines, including fibroblasts and endothelial and epithelial cells. In tissues, however, expression of adipophilin is restricted to certain cell types, such as lactating mammary epithelial cells, adrenal cortex cells, Sertoli and Leydig cells of the male reproductive system, and steatosis or fatty change hepatocytes in alcoholic liver cirrhosis (Heid 1998). Adipophilin has been reported to be overexpressed in colorectal cancer (Saha 2001), hepatocellular carcinoma (Kurokawa 2004), and in renal cell carcinoma (Young 2001).

c-Met encodes a heterodimeric transmembranous receptor with tyrosine kinase activity that is composed of an α-chain that is disulfide-linked to a β-subunit (Bottaro 1991; Rubin 1993). Both subunits are expressed on the surface, the heavy β-subunit is responsible for the binding of the ligand, hepatocyte growth factor (HGF), the α-subunit contains an intracellular domain that mediates the activation of different signal transduction pathways. c-Met signalling is involved in organ regeneration, as demonstrated for liver and kidney, embryogenesis, haematopoiesis, muscle development, and in the regulation of migration and adhesion of normally activated B-cells and monocytes (Zarnegar 1995; Naldini 1991; Montesano 1998; Schmidt 1995; Uehara 1995; Bladt 1995; Takayama 1996; Mizuno 1993; van, V 1997; Beilmann 2000). Furthermore, numerous studies indicated the involvement of c-Met overexpression in malignant transformation and invasiveness of malignant cells. c-Met mediates the multifunctional and potentially oncogenic activities of the HGF/scatter factor including promotion of cell growth, motility, survival, extracellular matrix dissolution, and angiogenesis (Bottaro 1991; Rubin 1993; Zarnegar 1995). Binding of HGF to the receptor induces autophosphorylation of c-Met and activates downstream signalling events including the ras, phosphatidylinositol 3'-kinase, phospholipase Cγ, and mitogen-activated protein kinase-related pathways. The c-Met gene is expressed predominantly in epithelial cells and is over-expressed in several malignant tissues and cell lines. An increasing number of reports have shown that nonepithelial cells such as haematopoietic, neural, and skeletal cells respond to HGF and haematological malignancies like multiple myeloma, Hodgkin disease, leukaemia, and lymphoma express the c-Met protein. Deregulated control of the invasive growth phenotype by oncogenically activated c-Met provoked by c-Met-activating mutations, c-Met amplification/over-expression, and the acquisition of HGF/c-Met autocrine loops confers invasive and metastatic properties to malignant cells. Notably, constitutive activation of c-Met in HGF-over-expressing transgenic mice promotes broad tumourigenesis.

Regulator of G-Protein Signalling 5 (RGS5) is a negative regulator of heterotrimeric G-protein signalling pathways, although its function in vivo remains elusive. RGS proteins comprise a family of molecules with a unifying catalytic function but varying tissue distribution. They stimulate the intrinsic guanosine triphosphatase (GTPase) activity of activated Gα subunits and thereby accelerate G-protein inactivation. Thus, RGS molecules inhibit signalling downstream of G-protein-coupled receptors (De 2000). Recently, it has been shown that Regulator of G-protein signaling-5 induction in pericytes coincides with active vessel remodelling during tumour neovascularization. In a mouse model of pancreatic islet cell carcinogenesis, as well as in highly angiogenic astrocytomas, overexpression of RGS5 has been shown in pericytes during the angiogenic switch accompanying active vessel remodelling. Overexpression was restricted to the tumour vasculature as compared to a normal islet of Langerhans. However, RGS5 is also upregulated during wound healing and ovulation (Berger 2005).

Expression of RGS5 is increased in RCC (Rae 2000). In another study, RT-PCR showed strong expression of RGS5 in all RCCs examined, and expression was very weak or undetectable in normal kidneys (6.6:1 by real-time PCR). Tumour endothelial cells were the main location of RGS5 in RCC (Furuya 2004). Furthermore, RGS5 was reported to be a sinusoidal endothelial cell marker in hepatocellular carcinoma (Chen 2004).

Apolipoprotein L1 (APOL1) is a secreted high density lipoprotein that binds to apolipoprotein A-I. Apolipoprotein A-I is a relatively abundant plasma protein and is the major apoprotein of HDL. It is involved in the formation of most cholesteryl esters in plasma and also promotes efflux of cholesterol from cells. Apolipoprotein L1 may play a role in lipid exchange and transport throughout the body, as well as in reverse cholesterol transport from peripheral cells to the liver. The plasma protein is a single chain polypeptide with an apparent molecular mass of about 40 kDa (Duchateau 1997; Duchateau 2001). APOL1 cDNA was isolated from an activated endothelial cell cDNA library and shown to be upregulated by TNF-α, which is a potent proinflammatory cytokine. (Monajemi 2002).

KIAA0367 was identified in the Kazusa cDNA Project that aims to identify unknown long human transcripts encoding putative proteins (Ohara 1997). Although the function of the putative 820 amino acid long protein product of KIAA0367 is unknown, it contains a CRAL-TRIO lipid binding domain profile at the C-terminus that binds small hydrophobic molecules and is present in several nucleotide exchange factors and in the BCL2/adenovirus E1B 19-kDa protein-interacting protein 2 (BNIP-2). BNIP-2 is involved in the control of diverse cellular functions including cell morphology, migration, endocytosis and cell cycle progression (Zhou 2005). KIAA0367 is located on the chromosomal region 9q21. This region is described as a common target of homozygous deletion in many tumours (Gursky 2001; Weber 2001) or loss of heterozygocity (Louhelainen 2000; Tripathi 2003).

Soluble guanylate cyclase (sGC), a heterodimeric protein consisting of an alpha and a beta subunit (1 heme-group), catalyzes the conversion of GTP to the second messenger cGMP and functions as the main receptor for nitric oxide and nitrovasodilator drugs (Zabel 1998). GUCYa3 and b3 are overexpressed in human gliomas. Transfection of antisense GUCY1A3 or GUCY1B3 reduced vascularisation and tumour growth in nude mice. This might be due to the fact that VEGF is induced by cGMP (Saino 2004). GUCY1A3 promotes tumour cell migration of a mice mammary tumor cell line (Jadeski 2003).

Cyclin D1 belongs to the highly conserved cyclin family, more specific to the cyclin D subfamily (Xiong 1991; Lew 1991). Cyclins function as regulators of CDKs (cyclin-dependent kinases). Different cyclins exhibit distinct expression and degradation patterns that contribute to the temporal coordination of each mitotic event (Deshpande 2005). Cyclin D1 forms a complex with- and functions as a regulatory subunit of CDK4 or CDK6, whose activity is required for cell cycle G1/S transition. CCND1 forms with CDK4 and CDK6 a serine/threonine kinase holoenzyme complex imparting substrate specificity to the complex (Bates 1994). The protein has been shown to interact with tumour suppressor protein Rb (Loden 2002) and the expression of this gene is regulated positively by Rb (Halaban 1999). Mutations, amplification and overexpression of this gene, which alters cell cycle progression, are observed frequently in a variety of tumours and may contribute to tumorigenesis (Hedberg 1999; Vasef 1999; Troussard 2000).

CSPG4 (chondroitin sulfate proteoglycan) represents an integral membrane chondroitin sulfate proteoglycan. It is known as an early cell surface melanoma progression marker implicated in stimulating tumor cell proliferation, migration and invasion. CSPG4 is strongly expressed on >90% of human melanoma lesions. Although CSPG4 is not strictly tumor specific, tumor-reactive CD4+ T-cell responses in melanoma patients and healthy individuals recognize $CSPG4_{693-709}$ on HLA-DR11-expressing melanoma cells in the absence of autoimmunity (Erfurt et al., 2007).

CSPG4 expression has also been described in some normal tissues besides activated pericytes such as endothelial cells, chondrocytes, smooth muscle cells, certain basal keratinocytes within the epidermis, as well as cells within the hair follicle (Campoli et al., 2004).

During angiogenesis and in response to CNS pathologies, the highly motile CSPG4 cells undergo rapid morphological changes and are recruited to sites where vessel growth and repair are occurring. CSPG4 is over-expressed by both tumor cells and pericytes on the blood vessels of malignant brain tumors (Chekenya and Pilkington, 2002). By implanting cells from an CSPG4-positive human glioma cell line into immunodeficient nude rat brains it was shown that these tumors had a higher microvascular density in comparison to controls implying that CSPG4 expression regulates both the function and the structure of the host-derived tumor vasculature (Brekke et al., 2006). In a xenograft experiment of implantation of GBM biopsy material into nude rats, CSPG4 was identified to be mainly associated with blood vessels on both the pericyte and basement membrane components of the tumor vasculature and the expression was also associated with areas of high cellular proliferation (Chekenya et al., 2002a). Furthermore, CSPG4 expression paralleled progression of the tumor in a glioma implantation model (Wiranowska et al., 2006).

CSPG4 is differentially expressed in human gliomas with higher expression in high grade gliolmas as compared to low-grade gliomas (Chekenya et al., 1999). High expression of CSPG4 correlates with multidrug resistance mediated by increased activation of α3β1 integrin/PI3K signaling and their downstream targets, promoting cell survival (Chekenya et al., 2008).

FABP7: Fatty acid-binding proteins (FABPs) are cytosolic 14-15 kDa proteins, which are supposed to be involved in fatty acid (FA) uptake, transport, and targeting. They are thought to increase the solubility of FAs in the cytoplasm when transporting FAs between membrane compartments, and bring FAs to their nuclear targets (Glatz et al., 2002). FABPs may modulate FA concentration and in this way influence various cellular functions such as enzymatic activity, gene expression, cellular growth and differentiation (Glatz and Storch, 2001).

FABP7 mRNA is expressed in tissues of neuroepithelial origin as well as in malignant glioma tumors (WHO grade III and IV). The gene was mapped to chromosome band 6q22-23, a region which also contains the proto-oncogene c-myc and frequently undergoes loss of heterozygosity in malignant glioma. Analysis of malignant glioma cell lines showed that FABP7 is often co-expressed with the glial fibrillary acidic protein (GFAP) suggesting that the cell of origin of malignant glioma may be an astrocytic precursor cell that has the potential of expressing both proteins normally or as the result of tumor formation (Godbout et al., 1998). FABP7 protein shows moderate to strong nuclear and cytoplasmic expression in GBM. FABP7-transfected glioma cells display 5-fold greater migration than control cells. Thus, the shorter overall survival associated with FABP7 over-expression especially in GBM may be due to increased migration and invasion of tumor cells into the surrounding brain parenchyma (Liang et al., 2005). Further analysis of FABP7 distribution in astrocytoma tumors indicates elevated levels of FABP7 in infiltrating regions of the tumors proposing an important role for FABP7 in driving the infiltration of malignant cells into adjacent brain tissues (Mita et al., 2007). FABP7 demonstrates variable expression levels and subcellular localization in glial tissues and all grades of astrocytoma. Nevertheless, nuclear localization of FABP7 seems to be especially associated with the infiltrative phenotype of glioma cells and EGFR pathways, as its nuclear translocation is detected after EGFR activation and is associated with poor prognosis in EGFR-positive GBM. Moreover, no nuclear FABP7 immunoreactivity can be observed in grade I astrocytoma (Liang et al., 2006; Kaloshi et al., 2007).

Neuroligin 4, X-linked is a member of a cell adhesion protein family that appears to play a role in the maturation and function of neuronal synapses. The members of the neuroligin family have a related structural organization, with an N-terminal signal peptide, the esterase-like domain with two sites of alternative splicing, a small linker region of low sequence identity in front of the transmembrane domain, and a short cytosolic part with a highly conserved C-Terminus Highest relative neuroligin 4 mRNA levels were found in heart. Lower expression was detected in liver, skeletal muscle and pancreas, whereas in brain, placenta, lung and kidney, neuroligin 4 mRNA was hardly detectable (Bolliger et al., 2001).

Mutations in the X-linked NLGN4 gene are a potential cause of autistic spectrum disorders, and mutations have been reported in several patients with autism, Asperger syndrome, and mental retardation (Jamain et al., 2003; Laumonnier et al., 2004; Lawson-Yuen et al., 2008).

Few associations of NLGN4X with cancer have been described: In gastrointestinal stromal tumors, over-expression of NLGN4X has been found in pediatric and young adult versus older adult cases (Prakash et al., 2005).

Tenascin C: The extracellular matrix surrounding tumor cells is different from the extracellular matrix in normal tissues. Tenascin-C (TNC) is an extracellular matrix protein that is highly up-regulated in processes that are closely associated with elevated migratory activity such as embryonic development (Bartsch et al., 1992), wound healing (Mackie et al., 1988) and neoplastic processes (Chiquet-Ehrismann, 1993; Chiquet-Ehrismann and Chiquet, 2003). Furthermore, TNC is over-expressed in tumor vessels that have a high proliferative index, which indicates that TNC is involved in neoplastic angiogenesis (Kim et al., 2000). In normal human brain, the expression of TNC is detected only rarely whereas it is expressed at high levels in malignant gliomas (Bourdon et al., 1983). TNC-expression can be induced by hypoxia (Lal et al., 2001), by TGF-beta1, providing a mechanism for the invasion of high-grade gliomas into healthy parenchyma (Hau et al., 2006), or by gastrin, which significantly modulates the migration of human GBM cells (Kucharczak et al., 2001). TNC down-regulates tropomyosin-1 and thus destabilizes actin stress fibers. It additionally causes down-regulation of the Wnt inhibitorDKK1. As reduced tropomyosin-1 expression and increased Wnt signaling are closely linked to transformation and tumorigenesis, TNC specifically modulates these signaling pathways to enhance proliferation of glioma cells (Ruiz et al., 2004).

Perivascular staining of TNC around tumor-supplying blood vessels is observed in GBM tissues, whereas it is less frequent in WHO grade II and III gliomas, indicating that the intensity of TNC staining correlates with the tumor grade and the strongest staining indicates poor prognosis (Herold-Mende et al., 2002). TNC also contributes to the generation of a stem cell niche within the subventricular zone (SVZ), acting to orchestrate growth factor signaling to accelerate neural stem cell development. The predominant effect of TNC on cells in the SVZ is the regulation of developmental progression (Garcion et al., 2004). TNC is the strongest inducer of directed human neural stem cell (NSC) migration. The tumor-produced ECM thus provides a permissive environment for NSC tropism to disseminated tumor cells (Ziu et al., 2006).

NRCAM (neuronal cell adhesion molecule) is a neuronal transmembrane cell adhesion molecule with multiple immunoglobulin-like C2-type and fibronectin type-III domains. It is involved in the guidance, outgrowth, and fasciculation of neuronal cells (Grumet et al., 1991; Morales et al., 1993; Stoeckli and Landmesser, 1995; Perrin et al., 2001; Sakurai et al., 2001) by forming homophilic, as well as heterophilic interactions with other IgCAMs (Volkmer et al., 1996; Sakurai et al., 1997; Zacharias et al., 1999). The ankyrin-binding NRCAM (Davis and Bennett, 1994) is upregulated in tube forming endothelial cells suggesting a possible role in tube formation and angiogenesis (Aitkenhead et al., 2002).

NRCAM is a target gene of the β-catenin and plakoglobin-LEF/TCF complex that contributes to oncogenesis (Conacci-Sorrell et al., 2002). The NRCAM ectodomain can be shed from the cell surface by metalloprotease-like activities. This shed domain is able to activate various signaling pathways, enhances cell motility, and confers tumorigenesis in mice (Conacci-Sorrell et al., 2005).

NRCAM is upregulated in anaplastic astrocytomas and GBM tumor tissues as compared to normal brain, and increased levels are correlated with the invasive behavior (Sehgal et al., 1998). Antisense RNA against NRCAM decreases the tumorigenic capacity of human GBM cells (Sehgal et al., 1999).

IGF2BP3 is a member of the insulin-like growth factor-II mRNA-binding protein family, implicated in mRNA localization, turnover and translational control. The protein contains several KH (K-homologous) domains, which are important in RNA binding and are known to be involved in RNA synthesis and metabolism. Expression occurs mainly during embryonic development and has been described for some tumors. Thus, IGF2BP3 is considered to be an oncofetal protein (Liao et al., 2005). The presence of high transcript levels of IGF2BP3 in numerous cancer tissues as compared to control tissues indicates that the IGF2BP3 protein might play a functional role in proliferating transformed cells. This hypothesis is supported by the finding that the only non-malignant human tissue expressing the IGF2BP3 transcript is human placenta, a tissue characterized by cell growth and proliferation (Mueller-Pillasch et al., 1997).

For example IGF2BP3 is expressed in clear cell RCC specimen and its expression is associated with advanced stage and grade of primary tumors. Furthermore, positive IGF2BP3 expression is associated with a 5-10 fold increased risk of distant metastases and with a 42%-50% increase in the risk of death from RCC (Hoffmann et al., 2008; Jiang et al., 2006; Jiang et al., 2008).

IGF2BP3 is also highly expressed in pancreatic carcinomas. In 2 studies >90% of pancreatic tumor tissue samples showed IGF2BP3 expression after immunostaining whereas non-neoplastic pancreatic tissues were negative for IGF2BP3. Furthermore, the expression increased progressively with tumor stage (Yantiss et al., 2005; Yantiss et al., 2008).

IGF2BP3 expression was also found to be significantly increased in high-grade urothelial tumors while it is generally not expressed in benign urothelium or low-grade urothelial tumors. Moreover, patients with IGF2BP3-positive tumors have a much lower progression-free survival and disease-free survival rate than those with IGF2BP3-negative tumors (Li et al., 2008; Sitnikova et al., 2008; Zheng et al., 2008).

Brevican (BCAN) is a brain-specific member of the lectican family of chondroitin sulfate proteoglycans. Two BCAN isoforms have been reported: a full-length isoform that is secreted into the extracellular matrix and a shorter isoform with a sequence that predicts a glycophosphatidylinositol (GPI) anchor. The secreted isoform is highly expressed from birth through 8 years of age and is downregulated by 20 years of age to low levels that are maintained in the normal adult cortex. The GPI isoform is expressed at uniformly low levels throughout development (Gary et al., 2000). BCAN belongs to a family of proteoglycans usually described as barrier molecules that prevent cell and neurite motility in the adult nervous system (Viapiano and Matthews, 2006). In vivo, BCAN is expressed around the boundaries of the rostral migratory stream (Jaworski and Fager, 2000) and is a major upregulated component of the glial scar after neural injury (Jaworski et al., 1999).

BCAN shows dramatic upregulation in gliomas, where an approximately seven-fold increase in expression over normal levels can be detected. BCAN mRNA was not detected in samples of adult human cortex from individuals who died without neurological complications. In sharp contrast, BCAN mRNA was detected in every one of 27 surgical samples of human glioma, thus suggesting that BCAN might be a unique and selective marker in glioma (Jaworski et al., 1996).

Protein Tyrosine Phosphatase, Receptor-Type, Zeta1 (PT-PRZ1, PTP-ξ)-PTPRZ1 is a member of the receptor type protein tyrosine phosphatase family and encodes a single-pass type I membrane protein with two cytoplasmatic tyrosine-protein phosphatase domains, an alpha-carbonic anhydrase domain and a fibronectin type-III domain. Expression of this gene is induced in gastric cancer cells (Wu et al., 2006), in breast cancer (Perez-Pinera et al., 2007), in the remyelinating oligodendrocytes of multiple sclerosis lesions (Harroch et al., 2002), and in human embryonic kidney cells under hypoxic conditions (Wang et al., 2005).

Both the protein and transcript are overexpressed in glioblastoma cells, promoting their haptotactic migration (Lu et al., 2005), and genomic DNA amplification in glioblastoma (Mulholland et al., 2006).

Chitinase 3-Like 2 (CHI3L2)-CHI3L2 was originally identified from chondrocytes and is upregulated e.g. in osteoarthritis (Steck et al., 2002). Although the protein is not well characterized yet, it is most likely secreted into the extracellular space. It has been frequently described as a target antigen in rheumatoid arthritis. Experimental anti-angiogenesis induction by siRNA transfection (VEGF-A) of a human glioma cell line caused upregulation of CHI3L2.

Survivin (BIRCS)—Expression of BIRCS (survivin), a member of the inhibitor of apoptosis protein (IAP) family, is elevated in fetal tissues and in various human cancers. Survivin seems to be capable of regulating both cellular proliferation and apoptotic cell death. Especially in glioblastoma, very high levels of survivin expression are detectable (Angileri et al., 2008). It is suggested that survivin overexpression in brain gliomas might play an important role in malignant proliferation, anti-apoptosis and angiogenesis (Zhen et al., 2005; Liu et al., 2006). Especially for glioblastoma, but also for other tumor entities, survivin expression was significantly associated with malignancy grade (with highest survivin expression in glioblastoma) and shorter overall survival times compared with patients who had survivin-negative tumors (Kajiwara et al., 2003; Saito et al., 2007; Uematsu et al., 2005; Mellai et al., 2008; Grunda et al., 2006; Xie et al., 2006; Sasaki et al., 2002; Chakravarti et al., 2002).

Proteins of the matrix metalloproteinase (MMP) family are involved in the breakdown of extracellular matrix in normal physiological processes, such as embryonic development, reproduction, and tissue remodelling, as well as in disease processes, such as arthritis and metastasis (Mott 2004). Matrix metalloproteinase 7 (MMP7) is secreted as an inactive pro-protein of 29.6 kDa that is activated when cleaved by extracellular proteinases. The active enzyme has a molecular weight of 19.1 kDa and binds two zinc ions and two calcium ions per subunit (Miyazaki 1990; Browner 1995). MMP7 degrades gelatins, fibronectin and casein (Miyazaki 1990; Quantin 1989) and differs from most MMP family members in that it lacks a conserved C-terminal protein domain (Gaire 1994). MMP7 is often found overexpressed in malignant tissue (Lin 2004; Bramhall 1997; Denys 2004) and it is suggested that it facilitates tumour cell invasion in vivo (Wang 2005).

These proteins can be the target of a tumour specific immune response in multiple types of cancer.

The Hepatitis B Virus Core Antigen peptide HBV-001 is not derived from an endogenous human tumour-associated antigen, but is derived from the Hepatitis B virus core antigen. First, it allows quantitative comparison of the magnitude of T-cell responses induced by tumor associated peptides (TU-MAPs) used in the pharmaceutical compositions of the present invention and hence allows one to study their ability to elicit anti-tumour responses. Second, it functions as an important positive control in the event of a lack of any T-cell responses in the patient. Third, it also allows monitoring of the immunocompetence of the patient.

Hepatitis B virus (HBV) infection is among the leading causes of liver disease, affecting approximately 350 million people world-wide (Rehermann 2005). Due to the ease of horizontal and vertical transmission and the potential for chronic disease that may lead to liver cirrhosis and hepatocellular carcinoma, HBV represents a major impact on the public health system for many countries worldwide. The HBV genome (Previsani 2002) is comprised of partially double-stranded circular DNA. In HBV virions, the DNA is packed together with the core protein HBc and other proteins to form the nucleocapsid, which is surrounded by an outer envelope containing lipids and the surface protein family HBs (also called envelope protein). The antigenic determinants that are associated with HBc and HBs are noted as HBcAg and HBsAg, respectively. These antigens are associated with serological, i.e. antibody responses found in the patient blood and are among the clinically most useful antigen-antibody systems for the diagnosis of HBV infection. HBc will represent a novel foreign antigen for all individuals without prior history of HBV infection. As immunogenic peptides are well known for this antigen (Bertoletti 1993; Livingston 1997), one ten-amino acid peptide from HBcAg was selected as a positive control antigen within IMA. The induction of HBc peptide-specific CTLs will then be used as a marker for patient immunocompetence and successful vaccination.

Pharmaceutical compositions of the present invention may be used for parenteral administration, such as subcutaneous, intradermal, intraperitoneal, intravenous, intramuscular or oral administration. For this, the peptides are dissolved or suspended in a pharmaceutically acceptable, preferably aqueous carrier. In addition, the composition can also contain excipients, such as antioxidants, preserving agents, buffers, binding agents, blasting agents, diluents, and flavours. The peptides can also be administered together with immune stimulating substances, such as cytokines. An extensive listing of excipients that can be used in such a composition, can be, for example, taken from A. Kibbe, Handbook of Pharmaceutical Excipients, 3. Ed., 2000, American Pharmaceutical Association and pharmaceutical press. Compositions of the invention can be used for a prevention, prophylaxis and/or therapy of adenomateous or cancerous diseases.

Pharmaceutical compositions of the present invention may be administered to a patient that suffers from an adenomateous or cancerous disease that is associated with the respective peptide or antigen of SEQ ID NO:1-10 or a patient that suffers from brain cancer, in particular, glioma, especially glioblastoma cancerous disease that is associated with the respective peptide or antigen of SEQ ID NO:11 to 22 or 11 to 23. The peptides in the pharmaceutical composition are able to trigger a T-cell-mediated immune response in the patient. As noted above, in case of renal cell cancer a pharmaceutical composition according to the present invention preferably comprises a peptide comprising the amino acid sequence set forth in SEQ ID NO:1 and/or SEQ ID NO:2 and further comprises at least one additional tumour associated peptide comprising the amino acid sequence set forth in SEQ ID NO: 3 to SEQ ID NO: 10. In the case of brain cancer, in particular glioma, especially glioblastoma cancer, the pharmaceutical composition preferably comprises a sequence set forth in SEQ ID NO:12 and/or SEQ ID NO:13 and further comprises at least one additional tumour associated peptide comprising the amino acid sequence set forth in SEQ ID NO: 11 and 14 to 22 and/or 23.

Preferably, peptides that are present in pharmaceutical compositions of the present invention have an overall length of between 9 and 100, preferably between 9 and 30, and most preferable between 9 and 16 amino acids. Furthermore, at least one peptide according to any of SEQ ID NO: 1 to SEQ ID NO: 23 can include non-peptide bonds.

A preferred pharmaceutical composition of the invention (preferably for the renal cell cancer vaccine) comprises a peptide consisting of the amino acid sequence set forth in SEQ ID NO: 1 and/or SEQ ID NO: 2, and in other embodiments further comprises at least one peptide consisting of the amino acid sequence set forth in SEQ ID NO: 3 to SEQ ID NO: 11.

A further preferred pharmaceutical composition of the invention (brain cancer, in particular glioma, especially glioblastoma cancer vaccine) comprises a peptide consisting of the amino acid sequence set forth in SEQ ID NO: 12 and/or SEQ ID NO: 13, and in other embodiments further comprises at least one peptide consisting of the amino acid sequence set forth in SEQ ID NO: 11 to SEQ ID NO: 22 and optionally SEQ ID NO: 23.

The peptide may also be tagged, or may be a fusion protein, or may be a hybrid molecule. The peptides whose sequence is given in the present invention are expected to stimulate $CD8^+$ CTL. However, stimulation is more efficient with the assistance from $CD4^+$ T-cells. Thus, the fusion partner or sections of a hybrid molecule suitably provide epitopes that stimulate $CD4^+$ T-cells. $CD4^+$ stimulating epitopes are well known in the art and include those identified in tetanus toxoid. In a further preferred embodiment the peptide is a fusion protein, in particular comprising N-terminal amino acids of the HLA-DR antigen-associated invariant chain (Ii). In one embodiment the peptide of the invention is a truncated human protein or a fusion protein of a protein fragment and another polypeptide portion provided that the human portion includes one or more amino acid sequences of the present invention.

Peptides useful in the pharmaceutical composition may be substantially pure, or combined with an immune-stimulating adjuvant, or used in combination with immune-stimulatory cytokines, or may be administered with a suitable delivery system, for example liposomes, micro-, nanoparticles, micelles, emulsions, gels. Peptide vaccination in general needs to be adjuvanted, and as such, GM-CSF is preferred (Human GM-CSF is commercially available as SARGRAMOSTIM®, LEUKINE®, available from Berlex now Bayer HealthCare Pharmaceuticals). Other suitable adjuvants include Aquila's QS21 STIMULON® (Aquila Biotech, Worcester, Mass., USA), which is derived from saponin, mycobacterial extracts and synthetic bacterial cell wall mimics, and proprietary adjuvants such as Ribi's DETOXT™. QUIL A™, another saponin derived adjuvant, may also be used (Superfos, Denmark). Other adjuvants such as Freund's may also be useful. It may also be useful to give the peptide conjugated to keyhole limpet hemocyanin (KLH) or mannan (see WO 95/18145 and Longenecker et al (1993) Ann. NY Acad. Sci. 690,276-291). Since an adjuvant is defined as a substance enhancing the immune response to an antigen (MEDLINEPLUS® Medical Dictionary, NIH) other substances with this function may be used, including, but not limited to, toll-like receptor agonists (TLR agonists), preferably substances that interact agonistically with TLR 3, 7, 8, and 9, such as protamine-stabilized RNA, CpG-oligonucleotides, CpR-oligonucleotides, bacterial DNA, and imidazoquinolines etc.

Other substances known in the art that are suitable to enhance an immune response include, but are not limited to, inhibitors of inducible nitric oxide synthase (iNOS), arginase (ARG1), indoleamine-2,3-dioxygenase (IDO), vascular endothelial growth factor receptor 1 (VEGFR-1), vascular endothelial growth factor (VEGF), cyclooxygenase-2 (COX-2), TGF-beta receptor I (TGF-beta-RI). Such inhibitors may be, for example, monoclonal antibodies against the molecules or small molecules. Small molecules and monoclonal antibodies known in the art to have an inhibitory function towards the factors mentioned above, and thus an immune response enhancing effect are, for example, 1-MT, NCX-4016, rofecoxib, CELEBREX®, BEC, ABH, nor-NOHA, SB-505124, SD-208, LY580276, AMD3100, axitinib, bevacizumab, JSI-124, CPA-7, XL-999, ZD2171, pazopanib, CP-547632, and VEGF Trap.

In addition, substances reducing the number of regulatory T-cells (CD 4+, CD25+, FoxP3+) are suitable as an adjuvants. These include, for example, but are not limited to cyclophosphamide (CYTOXAN®), ONTAK® (denileukin diftitox), Sunitinib, Sorafenib, anti-CTLA-4 (MDX-010, CP-675206), anti-CD25, anti-CCL22, and anti-GITR.

Preferred amounts of peptides in pharmaceutical compositions of the present invention may vary between about 0.1 and 100 mg, preferably between about 0.1 to 1 mg, and most preferably between about 300 µg to 800 µg per 500 µl of solution. The term "about" shall mean+/−10 percent of the given value, if not stated differently. The person of skill will be able to adjust the actual amount of peptide to be used based on several factors, such as, for example, the immune status of the individual patient and/or the amount of TUMAP that is presented in a particular type of cancer.

Pharmaceutical compositions of the present invention provide a formulation with an extremely enhanced solubility and the moistening of the lyophilisate over previously known compositions. This was achieved using a special composition of excipients. In this way, pharmaceutical compositions of the present invention comprising peptides of SEQ ID NO: 1 to 10 or SEQ ID NO: 1 to 11 and variants thereof were developed, which show a excellent shelf stability at (−20° C., +5° C., +25° C.) and can be easily resolubilized.

The term "shelf stability" means that the percentage of by-products does not rise more than 5% in two years. Furthermore the term "stability" means that the specific properties such as the solubility, the optical clarity of the solution and the number of particles in the solution do not change perceivable during that timeframe.

The term "easily resolubilized" shall mean that the lyophilisate can be completely dissolved through the use of a buffer or other excipients from seconds up to two minutes without the use of an of ultra sonic homogenizer. Furthermore the composition can be easily provided to a patient in need of treatment via i.d., and less preferably via s.c. The pH-value of the resulting solution should be between pH 2.7 and pH 9.

In another embodiment, a pharmaceutical composition of the present invention may include sugars, sugar alcohols, amino acids such a glycin, arginine, glutaminic acid and others as framework former. The sugars may be mono-, di- or trisaccharide. These sugars may be used alone, as well as in combination with sugar alcohols. Examples of sugars include glucose, mannose, galactose, fructose or sorbose as monosaccharides, saccharose, sucrose, lactose, maltose or trehalose as disaccharides and raffinose as a trisaccharid. A sugar alcohol may be, for example, mannitose. Preferred ingredients are saccharose, sucrose, lactose, maltose, trehalose, mannit and/or sorbit, and more preferably, mannitol.

Furthermore pharmaceutical compositions of the present invention may include physiological well tolerated excipients (see Handbook of Pharmaceutical Excipients, 5th ed., edited by Raymond Rowe, Paul Sheskey and Sian Owen, Pharmaceutical Press (2006)), such as antioxidants like ascorbic acid or glutathione, preserving agents such as phenole, m-cresole, methyl- or propylparabene, chlorobutanol, thiomersal or benzalkoniumchloride, stabilizer, framework former such as saccharose, sucrose, lactose, maltose, trehalose, mannitose, mannit and/or sorbit, mannit and/or lactose and solubilizer such as polyethyleneglycols (PEG), i.e. PEG 3000, 3350, 4000 or 6000, or cyclodextrines, i.e. hydroxypropyle-β-cyclodextrine, sulfobutylethyl-β-cyclodextrine or γ cyclodextrine, or dextranes or poloxaomers, i.e. poloxaomer 407°, poloxamer 188, or TWEEN 20® TWEEN 80®. In a preferred embodiment pharmaceutical compositions of the present invention include one or more well tolerated excipients, selected from the group consisting of antioxidants, framework formers and stabilizers.

The present invention relates to the finding that formulations including at least two sets of the peptides according to SEQ ID NO:1 to 10 or SEQ ID NO:1 to 11, mannitol and poloxamer 188 in a certain ratio lead to compositions that show greatly enhanced stability and can be dissolved without the use of ultra sonic treatment. Furthermore, solvation only requires a few seconds. Regarding the lyophilizate, a clear to opalescent solution should be observed by visual inspection after reconstitution with 4.2% sodium bicarbonate solution. These resolubilization characteristics of the pharmaceutical compositions of the present invention are reproducible even after storage of the drug product at −20° C., +5° C. and +25° C. for 2 years.

Furthermore, the present invention relates to formulations including at least four sets of the peptides according to the SEQ ID NO: 11 to SEQ ID NO: 22, SEQ ID NO: 11 to SEQ ID NO: 23, SEQ ID NO: 12 to SEQ ID NO: 22 or SEQ ID NO: 12 to SEQ ID NO: 23, wherein mannitol and poloxamer 188 in a certain ratio results in compositions that can be easily dissolved. Regarding the lyophilizate, a clear to opalescent solution should be observed by visual inspection after reconstitution with 4.2% sodium bicarbonate solution. The individual peptides in the described formulation are stable for at least 3 month after storage at −20° C., +5° C. and +25°.

In a preferred embodiment, pharmaceutical compositions of the present invention comprise a particular ratio of peptides:mannitol:TWEEN 80® (by weight), including and in the range of between 1:2:1.5 to 1:8:2.2. See the chart below for other preferred ratios, which are included in the present invention. An especially preferred ratio is 1:5:2. Another especially preferred ratio is 1:8:2.

In another preferred embodiment, pharmaceutical compositions of the present invention comprise a particular ratio of peptides:mannitol:poloxamer 188 (by weight), including and in the range of between 1:5:1.5 to 1:8:2.2. See the chart below for other preferred ratios, which are included in the present invention. A preferred ratio is 1:5:1.

Another especially preferred ratio of peptides:mannitol:poloxamer 188 by weight is 1:8:2. A more preferred composition includes a mixture of peptides:mannitol:Poloxamer 188® in a ratio of 1:5:2 by weight (see example 2). Another ratio includes peptides:mannitol:poloxamer 188 at a ratio of 1:0:2 to 1:2:2.2 by weight.

Other embodiments of the present invention include the following ratios by weight:

| Peptides | Mannitol | Poloxamer188 |
|---|---|---|
| 1 | 5 | 1.5 |
| 1 | 5 | 1.6 |
| 1 | 5 | 1.7 |

-continued

| Peptides | Mannitol | Poloxamer188 |
|---|---|---|
| 1 | 5 | 1.8 |
| 1 | 5 | 1.9 |
| 1 | 5 | 2 |
| 1 | 5 | 2.1 |
| 1 | 5 | 2.2 |
| 1 | 6 | 1.5 |
| 1 | 6 | 1.6 |
| 1 | 6 | 1.7 |
| 1 | 6 | 1.8 |
| 1 | 6 | 1.9 |
| 1 | 6 | 2 |
| 1 | 6 | 2.1 |
| 1 | 6 | 2.2 |
| 1 | 7 | 1.5 |
| 1 | 7 | 1.6 |
| 1 | 7 | 1.7 |
| 1 | 7 | 1.8 |
| 1 | 7 | 1.9 |
| 1 | 7 | 2 |
| 1 | 7 | 2.1 |
| 1 | 7 | 2.2 |
| 1 | 7.5 | 1.5 |
| 1 | 7.5 | 1.6 |
| 1 | 7.5 | 1.7 |
| 1 | 7.5 | 1.8 |
| 1 | 7.5 | 1.9 |
| 1 | 7.5 | 2 |
| 1 | 7.5 | 2.1 |
| 1 | 7.5 | 2.2 |
| 1 | 8 | 1.5 |
| 1 | 8 | 1.6 |
| 1 | 8 | 1.7 |
| 1 | 8 | 1.8 |
| 1 | 8 | 1.9 |
| 1 | 8 | 2 |
| 1 | 8 | 2.1 |
| 1 | 8 | 2.2 |
| 1 | 5.5 | 1.5 |
| 1 | 5.5 | 1.6 |
| 1 | 5.5 | 1.7 |
| 1 | 5.5 | 1.8 |
| 1 | 5.5 | 1.9 |
| 1 | 5.5 | 2 |
| 1 | 5.5 | 2.1 |
| 1 | 5.5 | 2.2 |
| 1 | 6.5 | 1.5 |
| 1 | 6.5 | 1.6 |
| 1 | 6.5 | 1.7 |
| 1 | 6.5 | 1.8 |
| 1 | 6.5 | 1.9 |
| 1 | 6.5 | 2 |
| 1 | 6.5 | 2.1 |
| 1 | 6.5 | 2.2 |
| 1 | 0 | 2 |
| 1 | 0 | 2.1 |
| 1 | 0 | 2.2 |
| 1 Preferred for preparation IMA950 | | |
| 1 | 5 | 0.5 |
| 1 | 5 | 0.6 |
| 1 | 5 | 0.7 |
| 1 | 5 | 0.8 |
| 1 | 5 | 0.9 |
| 1 | 5 | 1 |
| 1 | 5 | 1.1 |
| 1 | 5 | 1.2 |
| 1 | 5 | 1.3 |
| 1 | 5 | 1.4 |

| Peptide | Mannitol | TWEEN 80 ® |
|---|---|---|
| 1 | 2 | 1.5 |
| 1 | 2 | 1.6 |
| 1 | 2 | 1.7 |
| 1 | 2 | 1.8 |
| 1 | 2 | 1.9 |
| 1 | 2 | 2 |
| 1 | 2 | 2.1 |
| 1 | 2 | 2.2 |
| 1 | 3 | 1.5 |
| 1 | 3 | 1.6 |
| 1 | 3 | 1.7 |
| 1 | 3 | 1.8 |
| 1 | 3 | 1.9 |
| 1 | 3 | 2 |
| 1 | 3 | 2.1 |
| 1 | 3 | 2.2 |
| 1 | 4 | 1.5 |
| 1 | 4 | 1.6 |
| 1 | 4 | 1.7 |
| 1 | 4 | 1.8 |
| 1 | 4 | 1.9 |
| 1 | 4 | 2 |
| 1 | 4 | 2.1 |
| 1 | 4 | 2.2 |
| 1 | 5 | 1.5 |
| 1 | 5 | 1.6 |
| 1 | 5 | 1.7 |
| 1 | 5 | 1.8 |
| 1 | 5 | 1.9 |
| 1 | 5 | 2 |
| 1 | 5 | 2.1 |
| 1 | 5 | 2.2 |
| 1 | 6 | 1.5 |
| 1 | 6 | 1.6 |
| 1 | 6 | 1.7 |
| 1 | 6 | 1.8 |
| 1 | 6 | 1.9 |
| 1 | 6 | 2 |
| 1 | 6 | 2.1 |
| 1 | 6 | 2.2 |
| 1 | 7 | 1.5 |
| 1 | 7 | 1.6 |
| 1 | 7 | 1.7 |
| 1 | 7 | 1.8 |
| 1 | 7 | 1.9 |
| 1 | 7 | 2 |
| 1 | 7 | 2.1 |
| 1 | 7 | 2.2 |
| 1 | 8 | 1.5 |
| 1 | 8 | 1.6 |
| 1 | 8 | 1.7 |
| 1 | 8 | 1.8 |
| 1 | 8 | 1.9 |
| 1 | 8 | 2 |
| 1 | 8 | 2.1 |
| 1 | 8 | 2.2 |
| 1 | 2.1 | 1.5 |
| 1 | 2.1 | 1.6 |
| 1 | 2.1 | 1.7 |
| 1 | 2.1 | 1.8 |
| 1 | 2.1 | 1.9 |
| 1 | 2.1 | 2 |
| 1 | 2.1 | 2.1 |
| 1 | 2.1 | 2.2 |

The pharmaceutical compositions of the present invention may be lyophilized. The obtained lyophilisate can be reconstituted into a hydrous composition by adding a hydrous solvent. Preferably the hydrous composition would be able to be directly administered parenterally to a patient. Therefore, a further embodiment of the present invention is a hydrous pharmaceutical composition of the above disclosed formulations, obtainable through reconstitution of the lyophilisate described above with a hydrous solvent.

The acceptable pH-range is pH 2-12 for intravenous and intramuscular administration, but subcutaneously the range is reduced to 2.7-9.0 as the rate of in vivo dilution is reduced resulting in more potential for irritation at the injection site. Strickley Robert G., Pharm. Res., 21, NO:2, 201-230 (2004).

Preferably hydrous pharmaceutical composition of the invention have a pH-value from 7 to 9, even more preferred a pH-value from 8 to 9 and even more preferred a pH-value of 8.3 to 8.7.

Pharmaceutical compositions of the present invention are physiologically well tolerated, easily producible, exactly dosable, and show a excellent shelf stability concerning concentration, decomposition products and aggregates for the storing time. The preparations may be stable stored for 2 years in a freezer at −20° C., in a refrigerator at (+2-8° C.) and even at room temperature (+25° C.), 60% relative humidity.

Pharmaceutical compositions of the present invention are preferably sterile and formulated for in vivo administration.

The present invention also provides a method of raising an immune response in a subject, said method comprising administering to the subject in need thereof a pharmaceutical composition of the present invention, wherein said peptides, variants or salts are administered in an effective amount, preferably an amount effective to raise said immune response. The invention further provides the use of a pharmaceutical composition of the invention in a medicament for the administration to a subject to raise an immune response against cancer. Also included is the use of a pharmaceutical composition of the present invention for the treatment of cancer, preferably renal cancer, or brain cancer, preferably glioma and more preferably, glioblastoma and the use in the manufacture of a medicament for administration to a subject to raise an immune response against cancer and, thereby, to treat cancer.

Peptides used in the pharmaceutical composition are preferably pure, or essentially pure and, desirably, essentially homogeneous (i.e., free from contaminating peptides or proteins, etc.). "Essentially pure" means a peptide preparation with purity by HPLC of at least 90%, and preferably at least 95%. An "essentially homogeneous" preparation means a peptide preparation comprising at least 99% of the peptide, based on total weight of the peptide in the preparation.

The present invention furthermore includes a kit comprising:
(a) a container that contains a pharmaceutical composition as described above, in solution or in lyophilized form;
(b) optionally, a second container containing a diluent or reconstituting solution for the lyophilized formulation; and
(c) optionally, instructions for (i) use of the solution or (ii) reconstitution and/or use of the lyophilized formulation.

The kit may further comprise one or more of (i) a buffer, (ii) a diluent, (iii) a filter, (iv) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably, the kit and/or container contains instructions on or associated with the container that indicate directions for reconstitution and/or use. For example, the label may indicate that the lyophilized formulation is to be reconstituted to peptide concentrations as described herein. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have a distinct container for each component.

Preferably, kits of the invention include a formulation of the invention packaged for use in combination with the co-administration of a second compound (such as adjuvants (e.g. GM-CSF, a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. administration may be by infusion pump.

EXAMPLES

Example 1

Stock solutions of each individual peptide were prepared by dissolution of the peptides in appropriate solvents according to their solubilization characteristics (see Table 2). 1.47 mL of the higher concentrated peptide solutions (peptide 5 to 10) and 7.34 mL of the peptide solutions 1 to 4 were combined following by addition of 1.47 mL 10% acetic acid. The mixture was vortexed for 2 minutes and treated by ultrasonic bath for 1 minute. Approximately 1 mL of the resulting clear solution was transferred into glass vials, followed by addition of 19.2 mg mannitol and 50 μL of a TWEEN 80® stock solution (77 mg TWEEN 80® dissolved in 30% acetic acid solution). Within a few minutes the solution was frozen at −40° C. and lyophilized for 14 hours at 0.06 mbar, followed by 6 hours post drying period at 0.003 mbar (see Table 3).

TABLE 2

Peptides used for example 1.

| Peptide SEQ ID NO: | Peptide | Peptide content (%) | Amount [mg] | Solvent [ml] |
|---|---|---|---|---|
| 4 | IMA-CCN-001 | 95.5 | 16.65 | 7.57 (50% HAc) |
| 6 | IMA-GUC-001 | 88.8 | 17.72 | 7.50 (90% HAc) |
| 3 | IMA-ADF-001 | 91.7 | 17.35 | 7.58 (10% HAc) |
| 2 | IMA-ADF-002 | 94.0 | 16.95 | 7.58 (10% HAc) |
| 10 | IMA-RGS-001 | 89.4 | 17.66 | 1.50 (10% HAc) |
| 8 | IMA-MET-001 | 91.8 | 17.68 | 1.55 (50% HAc) |
| 9 | IMA-MUC-001 | 90.6 | 17.84 | 1.54 (10% HAc) |
| 1 | IMA-MMP-001 | 89.6 | 17.92 | 1.53 (WFI) |
| 4 | IMA-APO-001 | 92.1 | 17.76 | 1.56 (WFI) |
| 7 | IMA-K67-001 | 92.4 | 17.22 | 1.52 (WFI) |

TABLE 3

Lyophilisation parameters for example 1.

| Treatment | Time | Vacuum | Temperature |
|---|---|---|---|
| freezing | 3:00 | atm | −40° C. |
| primary drying | 0:10 | 0.06 mbar | −39° C. |
| primary drying | 3:00 | 0.06 mbar | −20° C. |
| primary drying | 10:00 | 0.06 mbar | +0° C. |
| primary drying | 6:00 | 0.06 mbar | +20° C. |
| secondary drying | 3:00 | 0.003 mbar | +20° C. |
| secondary drying | 6:00 | 0.003 mbar | +25° C. |

Example 2

A GMP lot was produced containing 2.000 vials with 578 µg per individual peptide per vial plus mannitol and Poloxamer 188. The formulation includes the peptides, mannitol and Poloxamer 188 in a ratio of 1:5:2 [w:w.w].

Each individual lyophilized peptide was weighed according to the amounts listed in Table 4 into separate glass vessels. After weighing, all peptides were dissolved in a specified solvent.

TABLE 4

Peptides used for example 2.

| Peptide SEQ ID NO: | Peptide | Net Amount [mg] | Peptide content [%] | Brutto Amount [mg] | Solvent [ml] |
|---|---|---|---|---|---|
| 4 | IMA-CCN-001 | 1156.00 | 91.6% | 1262.01 | 550 (50% HAc) |
| 6 | IMA-RGS-001 | 1156.00 | 83.2% | 1389.42 | 110 (10% HAc) |
| 3 | IMA-GUC-001 | 1156.00 | 92.9% | 1244.35 | 550 (90% HAc) |
| 2 | IMA-MET-001 | 1156.00 | 92.6% | 1248.38 | 110 (50% HAc) |
| 10 | IMA-ADF-001 | 1156.00 | 93.3% | 1239.01 | 540 (10% HAc) |
| 8 | IMA-ADF-002 | 1156.00 | 95.5% | 1210.47 | 540 (10% HAc) |
| 9 | IMA-MUC-001 | 1156.00 | 87.2% | 1325.69 | 110 (10% HAc) |
| 1 | IMA-MMP-001 | 1156.00 | 88.6% | 1304.74 | 110 (WFI) |

TABLE 4-continued

Peptides used for example 2.

| Peptide SEQ ID NO: | Peptide | Net Amount [mg] | Peptide content [%] | Brutto Amount [mg] | Solvent [ml] |
|---|---|---|---|---|---|
| 4 | IMA-APO-001 | 1156.00 | 95.0% | 1216.84 | 110 (WFI) |
| 7 | IMA-K67-001 | 1156.00 | 88.3% | 1309.17 | 110 (WFI) |

Due to the different solubilities of the peptides, they have to be dissolved according to the order provided in Table 4 beginning with peptide 1. Different amounts and concentrations of acetic acid solution and water for injection (WFI) were used for dissolving the peptides due to differences in the solubility of the peptides and with respect to the final filling volume of the bulk solution. For improving the solubility, each vial was treated by vigorous agitation for a maximum of five minutes and if necessary by sonification for a maximum of five minutes. The amounts and concentrations, to be used, are also shown in Table 4.

Once the peptides have been readily dissolved, the solutions have to be mixed in the order as given in Table 4, beginning with peptide number 1. The solutions are collected into a sterilized glass container. The individual peptide vials are rinsed with a solution of 105 ml acetic acid (30%). Finally, this solution is added to the mixture of the peptide solution and stirred for five minutes.

23.1 g Poloxamer 188 (LUTROL F68) and 57.8 g mannitol were added to the peptide mixture and the whole solution was stirred for five minutes.

The bulk solution containing all 10 peptides and the excipients was sterile-filtered through filter with pore size of 0.22 µm. 1.485 ml of the solution was filled into sterilized 2R glass vials under sterile conditions and under an inert nitrogen atmosphere, pre-sealed and transported into the freeze drier for lyophilization. The lyophilization process (see Table 5) includes freezing of the vials at temperature −45° C., a stepwise increase of temperature to +20° C. (Main drying phase) and a final drying step at +25° C. When the drying is complete, the freeze dryer was brought back to atmospheric pressure using dried nitrogen that has been sterile filtered.

TABLE 5

Lyophilisation parameter used for example 2.

| No. | Step | time [min] | T [° C.] | vacuum [mbar] |
|---|---|---|---|---|
| 1 | Loading | 3 | −45 | |
| 2 | Freezing | 180 | −45 | |
| 3 | Main drying | 15 | −45 | 1.50E−01 |
| 4 | Main drying | 300 | −20 | 1.50E−01 |
| 5 | Main drying | 480 | 0 | 1.50E−01 |
| 6 | Main drying | 360 | 20 | 1.50E−01 |
| 7 | Main drying | 60 | 20 | 1.50E−01 |
| 8 | After Drying | 15 | 2 | 5.00E−03 |
| 9 | After Drying | 180 | 20 | 5.00E−03 |
| 10 | After Drying | 120 | 25 | 5.00E−03 |
| 11 | After Drying | 240 | 25 | 5.00E−03 |
| 12 | pre-aeration | 1 | 25 | 8.00E+02 |
| 13 | Sealing | 5 | 25 | 8.00E+02 |
| 14 | Aeration with $N_2$ | 1 | 25 | 1.00E+03 |
| 15 | Storage | 3 | 5 | 1.00E+03 |

Resolubilization procedure: For clinical trials the above described formulation is dissolved in 700 µl sodium hydrogen carbonate (4.2%). Remove plastic cap from one vial. Unpack and remove sodium hydrogen carbonate (4.2%) from the refrigerator at least 30 min before resolubilization to bring them up to room temperature before injection. Prepare syringe and needle for reconstitution. Use aseptic technique to take 700 µL of diluent for reconstitution of the lyophilisate. To dissolve the lyophilisate, the vial and the diluent shall be shaken vigorously for 1 minute, check whether solution is clear, otherwise continue shaking for another minute until the solution is clear. 10 to 30 minutes after GM-CSF injection, use a new syringe to administer 500 µL reconstituted formulation i.d. at the same site. Administration has to occur within 1 h after reconstitution. Dissolved lyophilisate may be stored aseptically at room temperature for up to 1 hour following reconstitution.

Stability testing after reconstitution showed that most of the peptides remain sufficiently stable after reconstitution. However, a decrease of two specific peptides, i.e. IMA-CCN-001 and IMA-RGS-001 took place (see Table 6). As these peptides contain a cysteine residue, time-depending dimerization takes place.

TABLE 6

Results on HPLC-assay for in-use stability after reconstitution with 4.2% sodium hydrogen carbonate solution. Comparison between formulation with and without excipients.

| Peptide | Formulation | Initial* | 1 h | 2 h | 3 h | 4 h | 5 h | 6 h |
|---|---|---|---|---|---|---|---|---|
| ADF-001 | no excipients | 100.0 | 102.4 | 102.4 | 100.0 | n.d. | n.d. | n.d. |
|  | +mannitol/LUTROL ® | 100.0 | 99.6 | 99.6 | 100.7 | 100.8 | 99.9 | 101.8 |
| ADF-002 | no excipients | 100.0 | 100.9 | 100.0 | 97.2 | n.d. | n.d. | n.d. |
|  | +mannitol/LUTROL ® | 100.0 | 99.9 | 100.0 | 101.1 | 101.2 | 99.9 | 101.9 |
| APO-001 | no excipients | 100.0 | 100.0 | 97.4 | 97.4 | n.d.. | n.d. | n.d. |
|  | +mannitol/LUTROL ® | 100.0 | 99.8 | 99.8 | 100.7 | 100.9 | 99.6 | 101.5 |
| CCN-001 | no excipients | 100.0 | 82.8 | 72.1 | 63.3 | n.d. | n.d. | n.d |
|  | +mannitol/LUTROL ® | 100.0 | 95.6 | 92.2 | 91.3 | 89.2 | 86.1 | 85.9 |
| GUC-001 | no excipients | 100.0 | 100.0 | 100.0 | 98.6 | n.d. | n.d. | n.d. |
|  | +mannitol/LUTROL ® | 100.0 | 99.7 | 99.5 | 100.6 | 100.8 | 99.7 | 101.6 |
| K67-001 | no excipients | 100.0 | 100.8 | 99.2 | 97.5 | n.d. | n.d. | n.d. |
|  | +mannitol/LUTROL ® | 100.0 | 99.8 | 100.4 | 101.6 | 101.8 | 100.6 | 102.5 |
| MET-001 | no excipients | 100.0 | 100.0 | 99.2 | 96.7 | n.d. | n.d. | n.d. |
|  | +mannitol/LUTROL ® | 100.0 | 99.8 | 99.8 | 101.0 | 101.1 | 99.8 | 101.7 |
| MMP-001 | no excipients | 100.0 | 98.6 | 97.1 | 95.7 | n.d. | n.d. | n.d. |
|  | +mannitol/LUTROL ® | 100.0 | 99.5 | 99.3 | 100.2 | 100.4 | 98.9 | 100.9 |
| MUC-001 | no excipients | 100.0 | 100.8 | 99.2 | 96.6 | n.d. | n.d. | n.d. |
|  | +mannitol/LUTROL ® | 100.0 | 99.8 | 99.6 | 100.6 | 100.6 | 99.5 | 101.3 |
| RGS-001 | no excipients | 100.0 | 90.9 | 77.8 | 64.6 | n.d. | n.d. | n.d. |
|  | +mannitol/LUTROL ® | 100.0 | 97.9 | 95.5 | 94.2 | 91.6 | 88.0 | 86.8 |

*Starting value set to 100%. First HPLC run after resolubilization.

The influence of different pH values (around pH 8.5) and high capacity carbonate buffer on the success of peptide immunizations was assessed in a mouse model. Using a standard immunogenic model peptide in different injection solutions, the priming efficiency was tested by standard $^{51}$Cr release assay. Results were confirmed by flow cytometry analysis after tetramer staining. In summary, there was no significant difference detectable in priming efficiency between intradermal immunizations at pH 7.5, 8.5 (pH of the IMA901 diluent) and pH 9.5.

In addition, the high ionic strength did not reduce the observed immune response compared to isotonic injection buffer. Toxic side effects were not observed for immunizations with injection solutions at pH 7.5, 8.5, and with the IMA901 diluent, but became evident with the pH 9.5 injection solution (local necrotic lesions of the skin at the injection site). These results support the suitability of the chosen buffer as the appropriate diluent for IMA901.

Example 3

Stock solutions of each individual peptide were prepared by dissolution of the peptides in appropriate solvents according to there solubilization characteristics (see Table 7).

TABLE 7

Peptides used for example 3.

| Peptide NO: | Peptide | Peptide purity (%) | Amount [mg] | Solvent [ml] |
|---|---|---|---|---|
| 23 | IMA-CHI-001 | 99.7 | 23.19 | 11.560 (90% HAc) |
| 15 | IMA-FABP7-001 | 92.0 | 25.13 | 4.624 (90% HAc) |
| 17 | IMA-MET-005 | 93.1 | 24.83 | 3.853 (50% HAc) |
| 18 | IMA-NLGN4X-001 | 90.3 | 25.60 | 5.780 (50% HAc) |
| 22 | IMA-TNC-001 | 94.0 | 24.60 | 5.780 (30% HAc) |
| 20 | IMA-PTP-003 | 96.3 | 24.01 | 2.890 (20% HAc) |
| 12 | IMA-BCA-002 | 97.7 | 23.66 | 3.303 (10% HAc) |
| 13 | IMA-BIR-002 | 96.0 | 24.08 | 2.312 (10% HAc) |
| 14 | IMA-CSP-001 | 98.1 | 23.57 | 5.780 (10% HAc) |
| 16 | IMA-IGF2BP3-001 | 94.6 | 24.44 | 2.890 (10% HAc) |

TABLE 7-continued

Peptides used for example 3.

| Peptide NO: | Peptide | Peptide purity (%) | Amount [mg] | Solvent [ml] |
|---|---|---|---|---|
| 19 | IMA-NRCAM-001 | 96.0 | 24.08 | 2.312 (10% HAc) |
| 21 | IMA-PTP-005 | 97.0 | 23.84 | 2.312 (10% HAc) |
| 11 | IMA-HBV-001 | 99.0 | 23.35 | 4.624 (WFI) |
| —/— | Rinsing volume | —/— | —/— | 1.800 (30% HAc) |
| —/— | Fill up volume | —/— | —/— | 0.180 (WFI) |

Due to the different solubilities of the peptides, they have to be dissolved according to the order provided in Table 4 beginning with peptide 1. Different amounts and concentrations of acetic acid solution and water for injection (WFI) were used for dissolving the peptides due to differences in the solubility of the peptides and with respect to the final filling volume of the bulk solution. For improving the solubility, each vial was treated by vigorous agitation for a maximum of five minutes and if necessary by sonification for a maximum of five minutes. The amounts and concentrations, to be used, are also shown in Table 7.

Once the peptides have been readily dissolved, the solutions have to be mixed in the order as given in Table 7, starting with peptide number 1. The solutions are collected into a glass container equipped with a stirring bar. Finally, this solution is added to the mixture of the peptide solution and stirred at least for five minutes.

601.1 mg Poloxamer 188 (LUTROL F68®) and 1502.8 mg Mannitol were added to the peptide mixture and the whole solution was stirred for five minutes.

The bulk solution containing all 13 peptides and the excipients was sterile-filtered through filter with pore size of 0.22 µm. 1.500 ml of the solution was filled into 2R glass vials, pre-sealed and transported into the freeze drier for lyophilization. The lyophilization process (see Table 8) includes freezing of the vials at temperature −45° C., a stepwise increase of temperature to +20° C. (Main drying phase) and a final drying step at +25° C. When the drying is complete, the freeze dryer was brought back to atmospheric pressure using nitrogen.

TABLE 8

Lyophilisation parameters used for example 3.

| No. | Step | time [min] | T [° C.] | vacuum [mbar] |
|---|---|---|---|---|
| 1 | Loading | 5 | −45 | |
| 2 | primary drying | 10 | −45 | 0.50E−01 |
| 3 | primary drying | 360 | −20 | 0.50E−01 |
| 4 | primary drying | 480 | 0 | 0.50E−01 |
| 5 | primary drying | 360 | 20 | 0.50E−01 |
| 6 | primary drying | 60 | 20 | 0.50E−01 |
| 7 | secondary drying | 15 | 20 | 5.00E−03 |
| 8 | secondary drying | 180 | 20 | 5.00E−03 |
| 9 | secondary drying | 120 | 25 | 5.00E−03 |
| 10 | secondary drying | 240 | 25 | 5.00E−03 |
| 11 | Aeration with $N_2$ | 1 | 25 | 1.00E+03 |
| 12 | Sealing | 5 | 25 | 1.00E+03 |

Resolubilization Procedure:

For clinical trials the above described formulation is dissolved in 700 µl sodium hydrogen carbonate (4.2%). To dissolve the lyophilisate, the vial and the diluent shall be shaken vigorously for 1 minute, check whether solution is clear, otherwise continue shaking for another minute until the solution is clear. Administration of 500 µL of the solution has to occur within 1 h after reconstitution. Dissolved lyophilisate may be stored aseptically at room temperature for up to 1 hour following reconstitution.

Stability testing after reconstitution showed that most of the peptides remained sufficiently stable after reconstitution (see Table 9).

TABLE 9

Results on HPLC-assay for in-use stability after reconstitution with 4.2% sodium hydrogen carbonate solution. Comparison between formulation with and without excipients.

| Peptide | | Initial Peptide [%] | 2 h Peptide [%] | 4 h Peptide [%] | 6 h Peptide [%] |
|---|---|---|---|---|---|
| NRCAM-001 | +Mannitol/ LUTROL ® | 100.0 | 99.9 | 100.0 | 99.5 |
| | no excipients | 100.0 | 99.8 | 100.2 | 95.6 |
| BIR-002 | +Mannitol/ LUTROL ® | 100.0 | 100.8 | 101.2 | 100.9 |
| | no excipients | 100.0 | 100.6 | 101.4 | 96.2 |
| CSP-001 | +Mannitol/ LUTROL ® | 100.0 | 100.0 | 100.1 | 99.6 |
| | no excipients | 100.0 | 99.2 | 99.7 | 95.0 |
| PTP-003 | +Mannitol/ LUTROL ® | 100.0 | 100.3 | 100.5 | 100.1 |
| | no excipients | 100.0 | 100.4 | 100.9 | 96.1 |

TABLE 9-continued

Results on HPLC-assay for in-use stability after reconstitution with 4.2% sodium hydrogen carbonate solution. Comparison between formulation with and without excipients.

| Peptide | | Initial Peptide [%] | 2 h Peptide [%] | 4 h Peptide [%] | 6 h Peptide [%] |
|---|---|---|---|---|---|
| IGF2BP3-001 | +Mannitol/ LUTROL ® | 100.0 | 100.4 | 100.6 | 100.7 |
| | no excipients | 100.0 | 100.0 | 101.2 | 96.0 |
| PTP-005 | +Mannitol/ LUTROL ® | 100.0 | 100.1 | 100.3 | 99.8 |
| | no excipients | 100.0 | 99.9 | 100.4 | 95.8 |
| TNC-001 | +Mannitol/ LUTROL ® | 100.0 | 100.5 | 100.6 | 100.2 |
| | no excipients | 100.0 | 100.0 | 100.4 | 95.7 |
| MET-005 | +Mannitol/ LUTROL ® | 100.0 | 100.5 | 100.7 | 100.4 |
| | no excipients | 100.0 | 100.3 | 100.7 | 96.0 |
| FABP7-001 | +Mannitol/ LUTROL ® | 100.0 | 100.9 | 100.7 | 100.6 |
| | no excipients | 100.0 | 100.5 | 100.9 | 96.3 |
| NLGN4X-001 | +Mannitol/ LUTROL ® | 100.0 | 100.8 | 100.9 | 100.5 |
| | no excipients | 100.0 | 99.9 | 100.5 | 95.7 |
| HBV-001 | +Mannitol/ LUTROL ® | 100.0 | 100.3 | 100.6 | 100.3 |
| | no excipients | 100.0 | 100.2 | 100.6 | 95.8 |
| CHI-001 | +Mannitol/ LUTROL ® | 100.0 | 100.0 | 100.7 | 100.2 |
| | no excipients | 100.0 | 102.2 | 101.3 | 90.6 |
| BCA-002 | +Mannitol/ LUTROL ® | 100.0 | 99.8 | 99.6 | 98.9 |
| | no excipients | 100.0 | 99.9 | 100.1 | 95.4 |

Example 4

Stock solutions of each individual peptide were prepared by dissolution of the peptides in appropriate solvents according to there solubilization characteristics (see Table 10).

TABLE 10

Peptides used for example 4.

| Peptide SEQ ID NO: | Peptide | Peptide purity (%) | Amount [mg] | Solvent [ml] |
|---|---|---|---|---|
| 23 | IMA-FABP7-001 | 92.0 | 28.27 | 4.335 (90% HAc) |
| 15 | IMA-MET-005 | 94.0 | 27.67 | 4.335 (50% HAc) |
| 17 | IMA-NLGN4X-001 | 91.0 | 28.58 | 6.503 (50% HAc) |
| 18 | IMA-TNC-001 | 94.0 | 27.67 | 3.251 (50% HAc) |
| 22 | IMA-PTP-003 | 97.0 | 26.81 | 3.251 (20% HAc) |
| 20 | IMA-BCA-002 | 98.0 | 26.54 | 3.251 (10% HAc) |
| 12 | IMA-BIR-002 | 96.0 | 27.09 | 3.251 (10% HAc) |
| 13 | IMA-CSP-001 | 91.0 | 28.58 | 5.202 (10% HAc) |
| 14 | IMA-IGF2BP3-001 | 95.0 | 27.38 | 5.202 (10% HAc) |
| 16 | IMA-NRCAM-001 | 96.0 | 26.54 | 3.251 (10% HAc) |
| 19 | IMA-PTP-005 | 97.0 | 26.81 | 3.251 (10% HAc) |
| 21 | IMA-HBV-001 | 99.0 | 26.27 | 5.202 (WFI) |

TABLE 10-continued

Peptides used for example 4.

| Peptide SEQ ID NO: | Peptide | Peptide purity (%) | Amount [mg] | Solvent [ml] |
|---|---|---|---|---|
| —/— | Rinsing volume | —/— | —/— | 3.375 (30% HAc) |
| —/— | Fill up volume | —/— | —/— | 13.839 (WFI) |

Due to the different solubilities of the peptides, they have to be dissolved according to the order provided in Table 4 beginning with peptide 1. Different amounts and concentrations of acetic acid solution and water for injection (WFI) were used for dissolving the peptides due to differences in the solubility of the peptides and with respect to the final filling volume of the bulk solution. For improving the solubility, each vial was treated by vigorous agitation for a maximum of five minutes and if necessary by sonification for a maximum of five minutes. The amounts and concentrations, to be used, are also shown in Table 10.

Once the peptides had been readily dissolved, the solutions have to be mixed in the order as given in Table 10 beginning with peptide SEQ ID NO:23. The solutions are collected into a glass container equipped with a stirring bar. Finally, this solution is added to the mixture of the peptide solution and stirred at least for five minutes.

624.2 mg Poloxamer 188 (LUTROL F68®) and 1560.6 mg Mannitol were added to the peptide mixture and the whole solution was stirred for five minutes.

The bulk solution containing all 12 peptides and the excipients was sterile-filtered through filter with pore size of 0.22 µm. 1.500 ml of the solution was filled into 2R glass vials, pre-sealed and transported into the freeze drier for lyophilization. The lyophilization process (see Table 11) includes freezing of the vials at temperature −45° C., a stepwise increase of temperature to +20° C. (Main drying phase) and a final drying step at +25° C. When the trying is complete, the freeze dryer was brought back to atmospheric pressure using dried nitrogen.

TABLE 11

Lyophilisation parameter used for example 4.

| No. | Step | time [min] | T [° C.] | vacuum [mbar] |
|---|---|---|---|---|
| 1 | Loading | 5 | −45 | |
| 2 | primary drying | 10 | −45 | 0.50E−01 |
| 3 | primary drying | 360 | −20 | 0.50E−01 |
| 4 | primary drying | 480 | 0 | 0.50E−01 |
| 5 | primary drying | 360 | 20 | 0.50E−01 |
| 6 | primary drying | 60 | 20 | 0.50E−01 |
| 7 | secondary drying | 15 | 20 | 5.00E−03 |
| 8 | secondary drying | 180 | 20 | 5.00E−03 |
| 9 | secondary drying | 120 | 25 | 5.00E−03 |
| 10 | secondary drying | 240 | 25 | 5.00E−03 |
| 11 | Aeration with $N_2$ | 1 | 25 | 1.00E+03 |
| 12 | Sealing | 5 | 25 | 1.00E+03 |

Stability testing at different temperatures showed that all of the peptides are sufficiently stable even at stressed (+25° C.) conditions (see Table 12).

TABLE 12

Results on HPLC-assay for stability of peptides in formulation at +25° C. +/− 2° C. for 3 months.

| Peptide | INITIAL [%] | 1M [% of Initial] | 2M [% of Initial] | 3M [% of Initial] |
|---|---|---|---|---|
| NRCAM-001 | 100.0 | 97.90 | 96.73 | 97.59 |
| BIR-002 | 100.0 | 97.49 | 96.24 | 98.93 |
| CSP-001 | 100.0 | 98.04 | 96.99 | 98.71 |
| PTP-003 | 100.0 | 98.29 | 97.11 | 98.29 |
| IGF2BP3-001 | 100.0 | 98.01 | 96.77 | 97.34 |
| PTP-005 | 100.0 | 98.16 | 97.10 | 98.30 |
| TNC-001 | 100.0 | 97.86 | 96.80 | 97.21 |
| MET-005 | 100.0 | 97.49 | 96.13 | 97.21 |
| FABP7-001 | 100.0 | 98.43 | 97.71 | 98.67 |
| NLGN4X-001 | 100.0 | 97.90 | 96.30 | 96.41 |
| HBV-001 | 100.0 | 97.83 | 96.47 | 97.50 |
| BCA-002 | 100.0 | 98.20 | 97.05 | 97.88 |

TABLE 13

Results on HPLC-assay for stability of peptides in formulation at +5° C. +/− 3° C. for 3 months.

| Peptide | INITIAL [%] | 1M [% of Initial] | 2M [% of Initial] | 3M [% of Initial] |
|---|---|---|---|---|
| NRCAM-001 | 100.0 | 99.13 | 98.17 | 98.79 |
| BIR-002 | 100.0 | 98.53 | 97.28 | 100.01 |
| CSP-001 | 100.0 | 98.99 | 98.05 | 99.81 |
| PTP-003 | 100.0 | 99.07 | 97.95 | 98.68 |
| IGF2BP3-001 | 100.0 | 99.00 | 97.92 | 98.57 |
| PTP-005 | 100.0 | 98.93 | 97.79 | 98.67 |
| TNC-001 | 100.0 | 99.02 | 98.10 | 98.72 |
| MET-005 | 100.0 | 99.06 | 97.92 | 98.59 |
| FABP7-001 | 100.0 | 99.08 | 98.15 | 98.66 |
| NLGN4X-001 | 100.0 | 99.12 | 98.24 | 98.84 |
| HBV-001 | 100.0 | 98.87 | 97.76 | 98.47 |
| BCA-002 | 100.0 | 99.13 | 98.04 | 98.73 |

TABLE 14

Results on HPLC-assay for stability of peptides in formulation at −20° C. +/− 5° C. for 3 months.

| Peptide | INITIAL [%] | 1M [% of Initial] | 2M [% of Initial] | 3M [% of Initial] |
|---|---|---|---|---|
| NRCAM-001 | 100.0 | 99.23 | 97.86 | 98.91 |
| BIR-002 | 100.0 | 98.43 | 96.98 | 100.14 |
| CSP-001 | 100.0 | 98.99 | 97.61 | 99.61 |
| PTP-003 | 100.0 | 99.11 | 97.48 | 98.57 |
| IGF2BP3-001 | 100.0 | 99.10 | 97.54 | 98.42 |
| PTP-005 | 100.0 | 98.99 | 97.41 | 98.34 |
| TNC-001 | 100.0 | 99.01 | 97.61 | 98.57 |
| MET-005 | 100.0 | 99.14 | 97.54 | 99.00 |
| FABP7-001 | 100.0 | 99.09 | 97.60 | 98.39 |
| NLGN4X-001 | 100.0 | 99.05 | 97.60 | 98.62 |
| HBV-001 | 100.0 | 98.93 | 97.39 | 98.34 |
| BCA-002 | 100.0 | 99.17 | 97.61 | 98.61 |

Example 5

Analytical Test Procedure

Identity, purity and peptide content are determined by analytical RP-HPLC chromatography. Detection wavelength was 220 nm.
Testing of Stability (Stability of Test Formulations):
a) Renal Cell Cancer Vaccine:
Various lyophilisates were tested with respect to stability of each individual peptide at +25° C. and ±40° C. using an analytical HPLC assay. Stress tests at ±25° C. and ±40° C. were performed to determine trends as to which formulation is more stable at ambient and higher temperatures.

The peptides according to the SEQ ID NOs: 1 to 10 were lyophilised without any excipients and by addition of mannitol and Poloxamer 188 (LUTROL F68®) or TWEEN 80®.

The following test formulations were produced and stability were assessed at +25° C. and +40° C. by analytical HPLC assay:
Formulation 1: Peptides without any excipients;
Formulation 2: Peptides:mannitol:LUTROL F68® (Poloxamer 188) (1:5:2 by weight);
Formulation 3: Peptides:mannitol:TWEEN 80® (1:5:2 by weight); and
Formulation 4: Peptides:mannitol:TWEEN 80® (1:5:1 by weight).

Initial HPLC measurements have been performed for each formulation before storage in a climate chamber. For this purpose, the content of two vials was completely dissolved in 30% acetic acid and measured by RP-HPLC by repeat determination. To assure comparability between the individual measurements, B-Naphtyl-alanine was used as internal standard and lyophilized together with the peptides.

After 7, 14, 21, and 28 days, another two vials were removed from the climate chamber to assess stability.

Data assessment was performed by repeat determination of one vial. For one time point and temperature, two independent vials were used to obtain four data points in total. These values have been taken to calculate the standard deviation shown as error bars in the relevant diagram.

As a result of the experiments, the stability of each individual peptide of the formulation with mannitol and LUTROL F68® is comparable with the results obtained by the formulation without any excipients. Formulations containing TWEEN 80® show enhanced degradation of IMA-RGS-001 especially at +40° C. and an increase of the signal, especially for peptide IMA-ADF-001. This increase could be due to co-eluation of impurities caused by degradation of the peptides.

b) Glioblastoma Cell Cancer Vaccine:

Various lyophilisates were tested with respect to solubility and stability of the formulated peptides in the mixture.

The peptides according to the SEQ ID NOs: 11 to 23 were lyophilized without any excipients and with the addition of Mannitol/Poloxamer 188 (LUTROL F68®) and Mannitol/TWEEN 80®.

The following test formulations were produced, and their solubilities in different solutions and the stabilities at +25° C. and +40° C. were tested.
Formulation 1: Peptides without any excipients;
Formulation 2: Peptides:mannitol:LUTROL F68® (Poloxamer 188) (1:5:2 by weight);
Formulation 3: Peptides:mannitol:TWEEN 80® (1:5:2 by weight)

The stability of both formulations was equally good. The solubility was best using formulation two which gave a clear and colorless mixture, while formulation three in some instances exhibited a slight precipitation at higher concentrations. Using formulation one, no dissolution was possible at all.

As a result of the experiments, the stability of each individual peptide of the formulation with mannitol/LUTROL F68® and mannitol/TWEEN 80® is comparable with the results obtained by the formulation without any excipients. Without any excipient the formulation is not soluble in suitable solutions e.g. sodium hydrogen carbonate (4.2%).

Example 6

Calculation of Potency for Preparation IMA901

Effect of excipients Poloxamer 188 and mannitol on T-cell priming efficiency was tested. Non-active excipients in the IMA901 formulation are Poloxamer 188 (LUTROL F68®) and mannitol. These two excipients were not contained in the IMA901 formulation in the phase 1 trial and were included in the phase 2 trial formulation to enhance solubility and in-use stability of IMA901. In this study, the influence of these substances on T-cell priming efficiency in a mouse model was tested after peptide immunization with a murine model peptide. No toxic effects of Poloxamer 188 (LUTROL F68®) and mannitol were observed. T-cell priming was analyzed by tetramer staining and flow cytometry ex vivo nine days after immunization. The addition of Poloxamer® (LUTROL F68®)/mannitol to the immunization solution does not alter $CD8^+$ T cell priming efficiency.

Principle of Test

Immunization: For the priming of naïve $CD8^+$ T cells, the immunogenic $H2-K^b$ binding peptide $Ova_{257-264}$ (SIINFEKL) in combination with an adjuvant commonly used in mouse immunization (CpG deoxyoligonucleotide) in 4.2% bicarbonic buffer was injected intradermally into 8-12 weeks old female mice (strain C57BL/6, $H2^b$, 3 mice per group). Injection solutions with and without Poloxamer 188 (LUTROL F68® (16.5 mg/ml)) and mannitol (41.3 mg/ml) were compared. The concentrations of the excipients are the same as planned for the IMA901 injection solution. Positive controls were immunized subcutaneously with peptide solution containing CpG emulsified in TITERMAX® classic (Sigma-Aldrich).

Tetramer staining: After 9 days, mice were sacrificed and $Ova_{257-264}$-specific T cells in the spleen were analyzed ex vivo with tetramer staining and flow cytometry. The tetramer technology allows specific and sensitive detection of T-cells bearing the compatible T-cell receptor.

Results: No toxic effects of Poloxamer 188 (LUTROL F68 BASF, Ludwigshafen, Germany)/mannitol were observed locally at the injection sites or systemically. Positive control group, CpG group, and CpG/Poloxamer 188/mannitol group showed significantly higher frequencies of peptide-specific T-cells compared to the negative controls ($p<0.05$). There was no significant difference between the CpG only and the CpG/Poloxamer 188/mannitol group.

The possibility of artificially observed positive populations was excluded by tetramer-staining of the proliferated peptide-specific cells after five days in vitro stimulation with peptide (data not shown).

In conclusion, the presence of Poloxamer 188 (LUTROL F68®)/mannitol in the immunization cocktail does not alter peptide-triggered immune responses in mice, and therefore, adverse or unfavorable influences of Poloxamer 188 (LUTROL F68®) and mannitol on the efficacy and safety of peptide-based immunotherapeutics in general are not expected.

Materials and Methods

Peptides used for the manufacturing of the different formulations have been synthesized and supplied by Bachem AG, Switzerland.

The invention claimed is:

1. A pharmaceutical composition comprising:
   (a) at least 2 peptides; wherein said at least 2 peptides comprise SEQ ID NO: 5 and SEQ ID NO: 13, respectively; each peptide has a length of between 8 and 16 amino acids;
   wherein said peptides show a solubility in 90% acetic acid of at least 2.7 mg/mL; and
   (b) mannitol and poloxamer 188 or mannitol and polyoxyethylene (20) sorbitan monooleate, wherein the ratio by weight of said peptides to mannitol to poloxamer 188 is in the range including and between 1:5:1.5 to 1:8:2.2 or including and between 1:0:2 to 1:0:2.2; or wherein the ratio by weight of said peptides to mannitol to polyoxyethylene (20) sorbitan monooleate is in the range including and between 1:2:1.5 to 1:8:2.2.

2. The pharmaceutical composition of claim 1, wherein said ratio by weight of peptides to mannitol to poloxamer 188 is in the range including and between 1:0:2 to 1:0:2.2.

3. The pharmaceutical composition of claim 1, further comprising a peptide comprising an amino acid sequence selected from the group consisting of SEQ ID NO: 1-4 and 6-10; and comprising mannitol and poloxamer 188, wherein the ratio by weight of peptides to mannitol to poloxamer 188 ranges is in the range including and between 1:5:1.5 to 1:8:2.2 or including and between 1:0:2 to 1:0:2.2 wherein each peptide has a length of between 8 and 16 amino acids.

4. The pharmaceutical composition of claim 3, wherein the ratio by weight of peptides to mannitol to poloxamer 188 is in the range including and between 1:0:2 to 1:0:2.2.

5. The pharmaceutical composition of claim 1, further comprising a peptide comprising an amino acid sequence selected from the group consisting of SEQ ID NO: 1-4 and 6-10 and comprising mannitol and polyoxyethylene (20) sorbitan monooleate, wherein the ratio by weight of peptides to mannitol to polyoxyethylene (20) sorbitan monooleate is in the range including and between 1:2:1.5 to 1:8:2.2 wherein each peptide has a length of between 8 and 16 amino acids.

6. The pharmaceutical composition of claim 1, wherein said composition further comprises at least one peptide having an overall length of between 9 and 16 amino acids.

7. The pharmaceutical composition of claim 1, wherein at least one of said peptides includes non-peptide bonds.

8. The pharmaceutical composition of claim 1, wherein said at least 2 peptides present in the composition are tissue, cancer, and/or patient-specific.

9. The pharmaceutical composition of claim 1, further comprising at least one suitable adjuvant.

10. A kit comprising:
    (a) a container containing the pharmaceutical composition of claim 1, in solution or in lyophilized form;
    (b) optionally, a second container containing a diluent or reconstituting solution for said lyophilized formulation and/or at least one adjuvant; and
    (c) optionally, instructions for (i) use of the solution of (a), or (ii) reconstitution, and/or use of said lyophilized formulation, and
    (d) optionally further comprising one or more of (i) a buffer, (ii) a diluent, (iii) a filter, (iv) a needle, and (v) a syringe.

11. The pharmaceutical composition of claim 2, wherein at least one of said peptides includes non-peptide bonds.

12. The pharmaceutical composition of claim 1, wherein said composition further comprises at least one peptide consisting of the amino acid sequence selected from the group consisting of SEQ ID NO: 1 and SEQ ID NO: 2.

13. The pharmaceutical composition of claim 2, wherein said at least 2 peptides present in the composition are tissue, cancer, and/or patient-specific.

14. The pharmaceutical composition of claim 2, further comprising at least one suitable adjuvant.

15. A kit comprising:
    (a) a container containing a pharmaceutical composition of claim 2, in solution or in lyophilized form;
    (b) optionally, a second container containing a diluent or reconstituting solution for said lyophilized formulation and/or at least one adjuvant; and
    (c) optionally, instructions for (i) use of the solution of (a), or (ii) reconstitution, and/or use of said lyophilized formulation.

16. The pharmaceutical composition of claim 1, wherein said pharmaceutical formulation is stable for two years at −20° C.

17. The pharmaceutical composition of claim 1, wherein the pharmaceutical composition is a lyophilisate that can be completely dissolved in a 4.2% sodium bicarbonate solution within two minutes or less without the use of an ultrasonic homogenizer, and wherein at least one of the peptides has a solubility in 90% acetic acid of not more than 2.9 mg/mL.

* * * * *